US011918500B1

(12) United States Patent
Solotoff

(10) Patent No.: US 11,918,500 B1
(45) Date of Patent: Mar. 5, 2024

(54) HINGED KNEE BRACE WITH DOUBLE UPPER STRAP ARRANGEMENT

(71) Applicant: PREFERRED PRESCRIPTION, INC., Hollywood, FL (US)

(72) Inventor: Brandon Solotoff, Boca Raton, FL (US)

(73) Assignee: Preferred Prescription, Inc., Hollywood, FL (US)

( * ) Notice: Subject to any disclaimer, the term of this patent is extended or adjusted under 35 U.S.C. 154(b) by 196 days.

(21) Appl. No.: 17/210,539

(22) Filed: Mar. 24, 2021

Related U.S. Application Data

(60) Provisional application No. 63/002,456, filed on Mar. 31, 2020.

(51) Int. Cl.
*A61F 5/01* (2006.01)

(52) U.S. Cl.
CPC .... *A61F 5/0123* (2013.01); *A61F 2005/0137* (2013.01)

(58) Field of Classification Search
CPC .. A61F 5/00; A61F 5/01; A61F 5/0102; A61F 5/0104; A61F 5/0106; A61F 5/0109; A61F 5/0123; A61F 5/0132; A61F 2005/0132; A61F 2005/0165; A61F 2005/0137; A61F 13/00; A61F 13/06;
(Continued)

(56) References Cited

U.S. PATENT DOCUMENTS

| 58,403 A | 10/1866 | Goodwin |
| 634,437 A | 10/1899 | Braley et al. |
| 1,257,297 A | 2/1918 | Brown |

(Continued)

FOREIGN PATENT DOCUMENTS

| CN | 203915158 U | 11/2014 |
| CN | 105443565 B | 3/2016 |

(Continued)

OTHER PUBLICATIONS

Bracelayer Knee Stabilizing Compression Pants, "How to Stop Your Knee Brace from Slipping Down," Oct. 4, 2018; available at: https://usa.bracelayer.com/blogs/knee-news/how-to-stop-your-knee-brace-from-slipping-down.

(Continued)

*Primary Examiner* — Ophelia A Hawthorne
*Assistant Examiner* — Gina McCarthy
(74) *Attorney, Agent, or Firm* — Thomas A. O'Rourke; James Bongiorno

(57) ABSTRACT

A knee brace includes: an elastic sleeve, and first and second cinching straps. The sleeve includes: a first portion that encircles the leg of the wearer on a first side of the knee joint in proximity to the calf; and a second portion that encircles the leg of the wearer on a second side of the knee joint in proximity to the thigh region. The first and second cinching straps have first ends that are fixedly secured to a first side of the second portion of the elastic sleeve, and to a second side of the second portion of the elastic sleeve, respectively. The first and second cinching straps have a length to permit wrapping around the elastic sleeve at least one full circumferential loop in opposite directions. Flaps of material may be secured to the elastic sleeve to create sockets that receive arms of first and second polycentric hinges.

13 Claims, 18 Drawing Sheets

(58) Field of Classification Search
CPC .......... A61F 13/08; A61F 2013/00093; A61F 5/0125; A61F 5/24; A61F 13/12; A41D 13/065
See application file for complete search history.

(56) References Cited

U.S. PATENT DOCUMENTS

| | | | |
|---|---|---|---|
| 1,510,408 A | 9/1924 | Lychou | |
| 1,622,211 A | 3/1927 | Sheehan | |
| 2,144,641 A | 1/1939 | Snyder | |
| 2,195,024 A | 3/1940 | Bullock | |
| 2,270,685 A | 1/1942 | Miller | |
| 2,308,776 A | 1/1943 | Peckham | |
| 2,467,907 A | 4/1949 | Peckham | |
| 2,493,406 A * | 1/1950 | Hicks | A61F 5/24 128/118.1 |
| 2,587,166 A | 2/1952 | Jovick | |
| 2,959,168 A | 11/1960 | Shook | |
| 3,046,981 A | 7/1962 | Biggs | |
| 3,194,233 A | 7/1965 | Peckham | |
| 3,350,719 A | 11/1967 | McClure | |
| 3,528,412 A | 9/1970 | McDavid | |
| 3,575,166 A | 4/1971 | Rosman | |
| 3,581,741 A | 6/1971 | Rosman | |
| 3,587,572 A | 6/1971 | Evans | |
| 3,662,435 A | 5/1972 | Allsop | |
| 3,698,389 A | 10/1972 | Guedel | |
| 3,749,366 A | 7/1973 | Brucker | |
| 3,785,371 A | 1/1974 | Lewis | |
| 3,786,804 A * | 1/1974 | Lewis | A61F 5/0125 2/24 |
| 3,799,158 A | 3/1974 | Gardner | |
| 3,817,244 A | 6/1974 | Taylor | |
| 3,826,251 A | 7/1974 | Ross | |
| 3,853,123 A * | 12/1974 | Moore | A61F 5/0106 602/26 |
| 3,970,081 A | 7/1976 | Applegate | |
| 4,088,130 A * | 5/1978 | Applegate | A61F 5/0125 602/26 |
| 4,090,508 A | 5/1978 | Gaylord | |
| 4,116,236 A | 9/1978 | Albert | |
| 4,176,665 A | 12/1979 | Terpening | |
| 4,185,360 A | 1/1980 | Prete | |
| 4,201,203 A | 5/1980 | Applegate | |
| 4,215,687 A | 8/1980 | Shaw | |
| 4,219,892 A | 9/1980 | Rigdon | |
| 4,240,414 A | 12/1980 | Theisler | |
| 4,256,097 A | 3/1981 | Willis | |
| 4,271,831 A | 6/1981 | Deibert | |
| 4,275,716 A | 6/1981 | Scott | |
| 4,287,885 A | 9/1981 | Applegate | |
| 4,353,362 A * | 10/1982 | DeMarco | A61F 5/0109 D24/190 |
| 4,366,813 A | 1/1983 | Nelson | |
| 4,370,977 A | 2/1983 | Mauldin | |
| 4,370,978 A | 2/1983 | Palumbo | |
| 4,372,298 A | 2/1983 | Lerman | |
| 4,379,463 A * | 4/1983 | Meier | A61F 5/0123 602/26 |
| 4,381,768 A | 5/1983 | Erichsen | |
| D269,379 S | 6/1983 | Bledsoe | |
| 4,387,709 A | 6/1983 | Shen | |
| 4,428,369 A | 1/1984 | Peckham | |
| 4,433,679 A | 2/1984 | Mauldin | |
| 4,445,505 A | 5/1984 | Labour | |
| 4,487,200 A | 12/1984 | Feanny | |
| 4,493,316 A | 1/1985 | Reed | |
| 4,506,661 A | 3/1985 | Foster | |
| 4,520,804 A | 6/1985 | DiGeorge | |
| 4,523,585 A | 6/1985 | Lamb | |
| 4,524,764 A | 6/1985 | Miller | |
| 4,554,913 A | 11/1985 | Womack | |
| 4,556,053 A | 12/1985 | Irons | |
| 4,572,170 A | 2/1986 | Cronk | |
| 4,576,151 A | 3/1986 | Carmichael | |
| 4,604,770 A | 8/1986 | Lang | |
| 4,607,628 A | 8/1986 | Dashefsky | |
| 4,624,247 A | 11/1986 | Ford | |
| 4,628,916 A | 12/1986 | Lerman | |
| 4,632,096 A | 12/1986 | Harris | |
| 4,632,098 A | 12/1986 | Grundei | |
| 4,633,867 A | 1/1987 | Kausek | |
| 4,686,969 A | 8/1987 | Scott | |
| 4,726,362 A * | 2/1988 | Nelson | A61F 5/0123 602/26 |
| 4,732,143 A | 3/1988 | Kausek | |
| 4,738,252 A | 4/1988 | Friddle | |
| 4,751,920 A | 6/1988 | Mauldin | |
| 4,768,500 A | 9/1988 | Mason | |
| 4,791,916 A | 12/1988 | Paez | |
| 4,796,610 A | 1/1989 | Cromartie | |
| 4,803,975 A | 2/1989 | Meyers | |
| 4,805,606 A | 2/1989 | McDavid | |
| 4,817,588 A | 4/1989 | Bledsoe | |
| 4,822,371 A | 4/1989 | Jolly | |
| 4,838,251 A | 6/1989 | Chignon | |
| 4,846,842 A | 7/1989 | Connolly | |
| 4,854,308 A | 8/1989 | Drillio | |
| 4,856,501 A | 8/1989 | Castillo | |
| 4,870,956 A | 10/1989 | Fatool | |
| 4,872,448 A | 10/1989 | Johnson | |
| 4,928,670 A | 5/1990 | DeLorenzo | |
| 4,928,676 A | 5/1990 | Pansiera | |
| 4,938,207 A | 7/1990 | Vargo | |
| 4,940,044 A | 7/1990 | Castillo | |
| 4,955,369 A | 9/1990 | Bledsoe | |
| 4,961,416 A | 10/1990 | Moore | |
| 4,966,133 A | 10/1990 | Kausek | |
| 4,982,732 A | 1/1991 | Morris | |
| 4,986,264 A | 1/1991 | Miller | |
| 5,000,169 A | 3/1991 | Swicegood | |
| 5,009,223 A | 4/1991 | DeFonce | |
| 5,016,621 A | 5/1991 | Bender | |
| 5,018,514 A | 5/1991 | Grood | |
| 5,022,391 A | 6/1991 | Weidenburner | |
| 5,025,782 A | 6/1991 | Salerno | |
| 5,038,763 A | 8/1991 | Wiggins | |
| 5,039,247 A | 8/1991 | Young | |
| 5,042,464 A | 8/1991 | Skwor | |
| 5,060,640 A | 10/1991 | Rasmusson | |
| 5,062,858 A | 11/1991 | Broeck | |
| 5,063,913 A | 11/1991 | Nyi | |
| 5,063,916 A | 11/1991 | France | |
| 5,078,127 A | 1/1992 | Daneman | |
| 5,086,760 A | 2/1992 | Neumann | |
| 5,092,320 A | 3/1992 | Maurer | |
| 5,107,824 A | 4/1992 | Rogers | |
| 5,135,469 A | 8/1992 | Castillo | |
| 5,168,865 A | 12/1992 | Radcliffe | |
| 5,188,584 A | 2/1993 | Petrofsky | |
| 5,230,696 A | 7/1993 | Silver | |
| 5,267,946 A | 12/1993 | Singer | |
| 5,277,697 A | 1/1994 | France | |
| 5,277,698 A | 1/1994 | Taylor | |
| 5,288,287 A | 2/1994 | Castillo | |
| 5,302,169 A | 4/1994 | Taylor | |
| 5,330,418 A | 7/1994 | Townsend | |
| 5,352,190 A | 10/1994 | Fischer | |
| 5,356,370 A | 10/1994 | Fleming | |
| 5,358,469 A | 10/1994 | Patchel | |
| 5,383,843 A | 1/1995 | Watson | |
| 5,403,002 A | 4/1995 | Brunty | |
| 5,407,420 A | 4/1995 | Bastyr | |
| 5,409,449 A | 4/1995 | Nebolon | |
| 5,419,754 A | 5/1995 | Hutchins | |
| 5,421,810 A | 6/1995 | Davis | |
| 5,443,444 A | 8/1995 | Pruyssers | |
| 5,458,565 A | 10/1995 | Tillinghast | |
| 5,460,599 A | 10/1995 | Davis | |
| 5,472,410 A | 12/1995 | Hamersly | |
| 5,490,831 A | 2/1996 | Myers | |
| 5,527,268 A | 6/1996 | Gildersleeve | |
| 5,554,104 A | 9/1996 | Grim | |
| 5,558,627 A | 9/1996 | Singer | |

(56) References Cited

U.S. PATENT DOCUMENTS

| | | | |
|---|---|---|---|
| 5,586,970 A | 12/1996 | Morris | |
| 5,641,322 A | 6/1997 | Silver | |
| 5,658,243 A | 8/1997 | Miller | |
| 5,672,152 A | 9/1997 | Mason | |
| 5,743,865 A | 4/1998 | Townsend | |
| 5,782,785 A | 7/1998 | Herzberg | |
| 5,792,084 A | 8/1998 | Wilson | |
| 5,797,864 A | 8/1998 | Taylor | |
| 5,800,371 A | 9/1998 | Winn | |
| 5,807,294 A | 9/1998 | Cawley | |
| 5,814,000 A | 9/1998 | Kilby | |
| 5,817,040 A | 10/1998 | Hess | |
| 5,823,931 A | 10/1998 | Gilmour | |
| 5,857,989 A | 1/1999 | Smith | |
| 5,865,776 A | 2/1999 | Springs | |
| 5,865,777 A | 2/1999 | Detty | |
| 5,873,847 A | 2/1999 | Bennett | |
| 5,873,848 A | 2/1999 | Fulkerson | |
| 5,938,629 A | 8/1999 | Bloedau | |
| 5,997,493 A | 12/1999 | Young | |
| 6,074,355 A | 6/2000 | Bartlett | |
| 6,110,138 A | 8/2000 | Shirley | |
| 6,203,511 B1 | 3/2001 | Johnson | |
| 6,290,664 B1 | 9/2001 | Nauert | |
| 6,402,711 B1 | 6/2002 | Nauert | |
| 6,402,713 B1 | 6/2002 | Doyle | |
| 6,413,232 B1 | 7/2002 | Townsend | |
| 6,527,733 B1 | 3/2003 | Ceriani | |
| 6,540,709 B1 | 4/2003 | Smits | |
| 6,547,218 B2 | 4/2003 | Landy | |
| 6,610,023 B2 | 8/2003 | Steponovich | |
| 6,689,080 B2 | 2/2004 | Castillo | |
| 6,773,411 B1 | 8/2004 | Alvarez | |
| 6,878,126 B2 | 4/2005 | Nelson | |
| 6,993,808 B1 | 2/2006 | Bennett | |
| 6,994,682 B2 | 2/2006 | Bauerfeind | |
| 7,004,919 B2 | 2/2006 | Gaylord | |
| 7,037,287 B2 | 5/2006 | Cormier | |
| 7,059,329 B2 | 6/2006 | Mason | |
| 7,122,016 B1 | 10/2006 | DeToro | |
| 7,150,721 B2 | 12/2006 | Houser | |
| 7,189,212 B2 | 3/2007 | Popp | |
| 7,198,610 B2 | 4/2007 | Infimundarson | |
| 7,201,728 B2 | 4/2007 | Sterling | |
| 7,217,249 B2 | 5/2007 | Scott | |
| 7,235,059 B2 | 6/2007 | Mason | |
| 7,285,103 B2 | 10/2007 | Nathanson | |
| 7,306,572 B2 | 12/2007 | Ceriani | |
| D573,713 S | 7/2008 | Mueller | |
| 7,431,708 B2 | 10/2008 | Sreeramagiri | |
| 7,473,234 B1 | 1/2009 | Weltner | |
| 7,597,675 B2 | 10/2009 | Ingimundarson | |
| 7,615,021 B2 | 11/2009 | Nordt | |
| 7,691,074 B2 | 4/2010 | Nordt | |
| 7,704,218 B2 | 4/2010 | Einarsson | |
| 7,713,225 B2 | 5/2010 | Ingimundarson | |
| 7,794,418 B2 | 9/2010 | Ingimundarson | |
| 7,819,830 B2 | 10/2010 | Sindel | |
| 7,867,183 B2 | 1/2011 | Kazmierczak | |
| 7,892,195 B2 | 2/2011 | Grim | |
| 7,896,827 B2 | 3/2011 | Ingimundarson | |
| 7,984,531 B2 | 7/2011 | Moore | |
| 7,988,653 B2 | 8/2011 | Fout | |
| 8,016,781 B2 | 9/2011 | Ingimundarson | |
| D646,790 S | 10/2011 | Castillo | |
| 8,062,242 B2 | 11/2011 | Ceriani | |
| 8,104,141 B2 | 1/2012 | Yamashita | |
| 8,172,781 B2 | 5/2012 | Oddou | |
| 8,231,560 B2 | 7/2012 | Ingimundarson | |
| 8,241,234 B2 | 8/2012 | Ingimundarson | |
| 8,257,293 B2 | 9/2012 | Ingimundarson | |
| 8,277,401 B2 | 10/2012 | Hammerslag | |
| 8,591,444 B2 | 11/2013 | Bejarano | |
| 8,728,018 B2 | 5/2014 | McCune | |
| 8,808,211 B2 | 8/2014 | Paulos | |
| 8,858,482 B2 | 10/2014 | Ingimundarson | |
| 8,864,692 B2 | 10/2014 | Ingimundarson | |
| 8,865,962 B2 * | 10/2014 | Weidemann-Hendrickson | A61F 13/12 602/53 |
| 8,882,689 B2 | 11/2014 | Castillo | |
| 8,926,539 B2 | 1/2015 | Cropper | |
| 9,125,730 B2 | 9/2015 | Ingimundarson | |
| 9,265,645 B2 | 2/2016 | Ingimundarson | |
| 9,351,864 B2 | 5/2016 | Romo | |
| 9,458,878 B2 | 10/2016 | Scatassa | |
| 10,143,581 B2 | 12/2018 | Chetlapalli | |
| 2003/0149386 A1 | 8/2003 | Ceriani | |
| 2003/0204156 A1 * | 10/2003 | Nelson | A61F 5/0123 602/26 |
| 2004/0153017 A1 * | 8/2004 | Simmons | A61F 5/0109 602/26 |
| 2004/0225245 A1 | 11/2004 | Nelson | |
| 2004/0267179 A1 | 12/2004 | Lerman | |
| 2005/0192523 A1 | 9/2005 | Knecht | |
| 2006/0100561 A1 | 5/2006 | Gilmour | |
| 2006/0206045 A1 | 9/2006 | Townsend | |
| 2007/0010772 A1 | 1/2007 | Ryan | |
| 2007/0213648 A1 | 9/2007 | Ferrigolo | |
| 2009/0131844 A1 | 5/2009 | Dean | |
| 2009/0259154 A1 | 10/2009 | Nace | |
| 2009/0287128 A1 | 11/2009 | Inglmundarson | |
| 2009/0299244 A1 | 12/2009 | Chiang | |
| 2011/0000097 A1 | 1/2011 | Chan | |
| 2013/0190669 A1 | 7/2013 | Rokosz | |
| 2014/0124557 A1 | 5/2014 | Velare | |
| 2014/0148747 A1 | 5/2014 | Fleming | |
| 2016/0040464 A1 | 2/2016 | Lu | |

FOREIGN PATENT DOCUMENTS

| | | |
|---|---|---|
| DE | 19904554 B4 | 8/2000 |
| DE | 60035431 T2 | 3/2008 |
| DE | 102012002554 A1 | 8/2013 |
| EP | 2260799 A1 | 12/2010 |
| EP | 3378448 A2 | 9/2018 |
| GB | 2136294 A | 9/1984 |
| GB | 2163352 A | 2/1986 |
| KR | 20180082516 A | 7/2018 |

OTHER PUBLICATIONS

Shalmali Pal, Lower Extremity Review Magazine, "Minimizing the Effects of Knee Brace Migration," Jun. 2012, available at: https://lermagazine.com/article/minimizing-the-effects-of-knee-brace-migration.

Press Fit Forces Stress Design Calculator, Jun. 18, 2018, available at: www.engineersedge.com/calculators/machine-design/press-fit/press-fit.htm.

"Three General Types of Fit," available at www.mmto.org/dclark/Reports/Encoder%20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

* cited by examiner

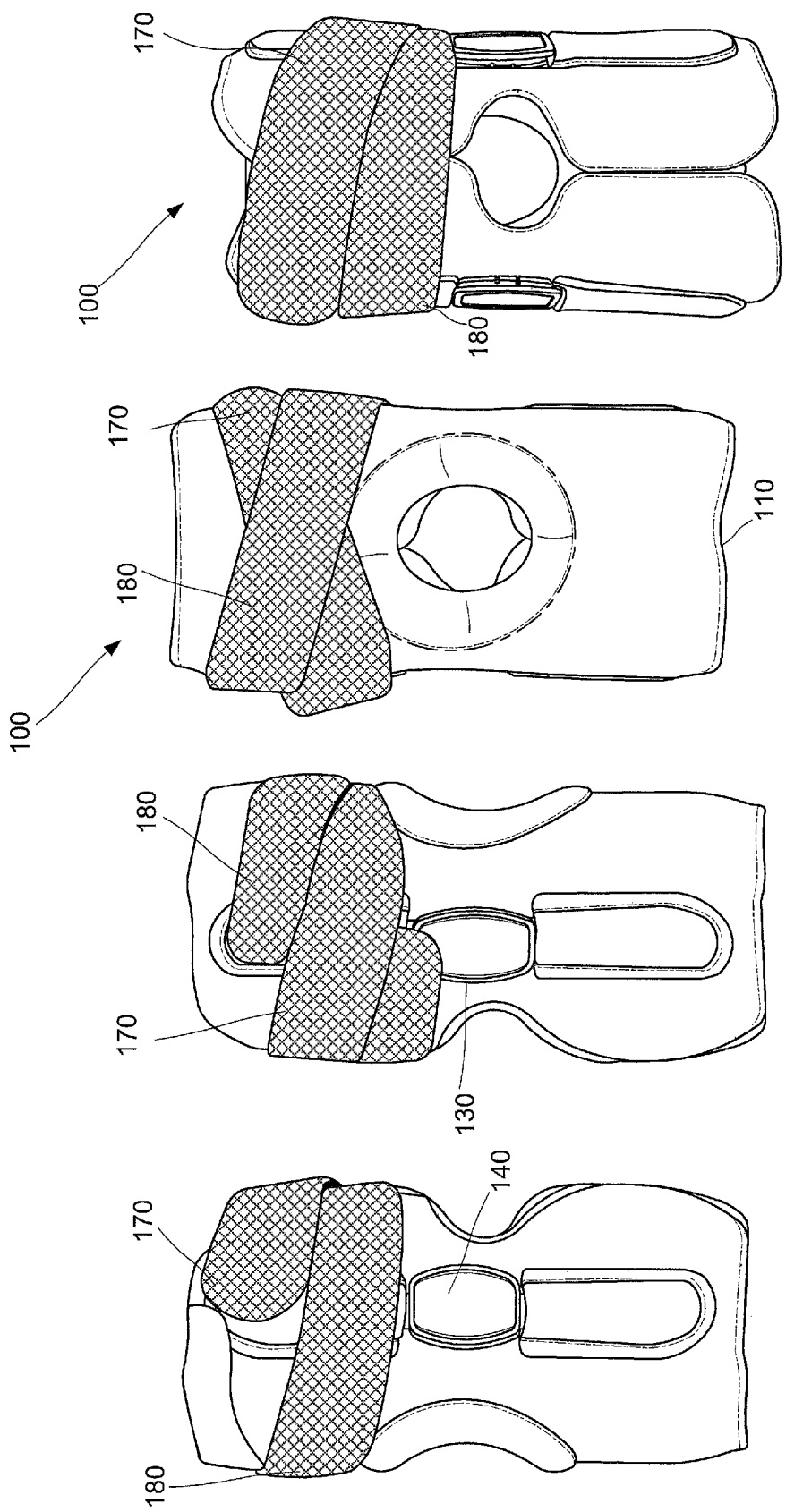

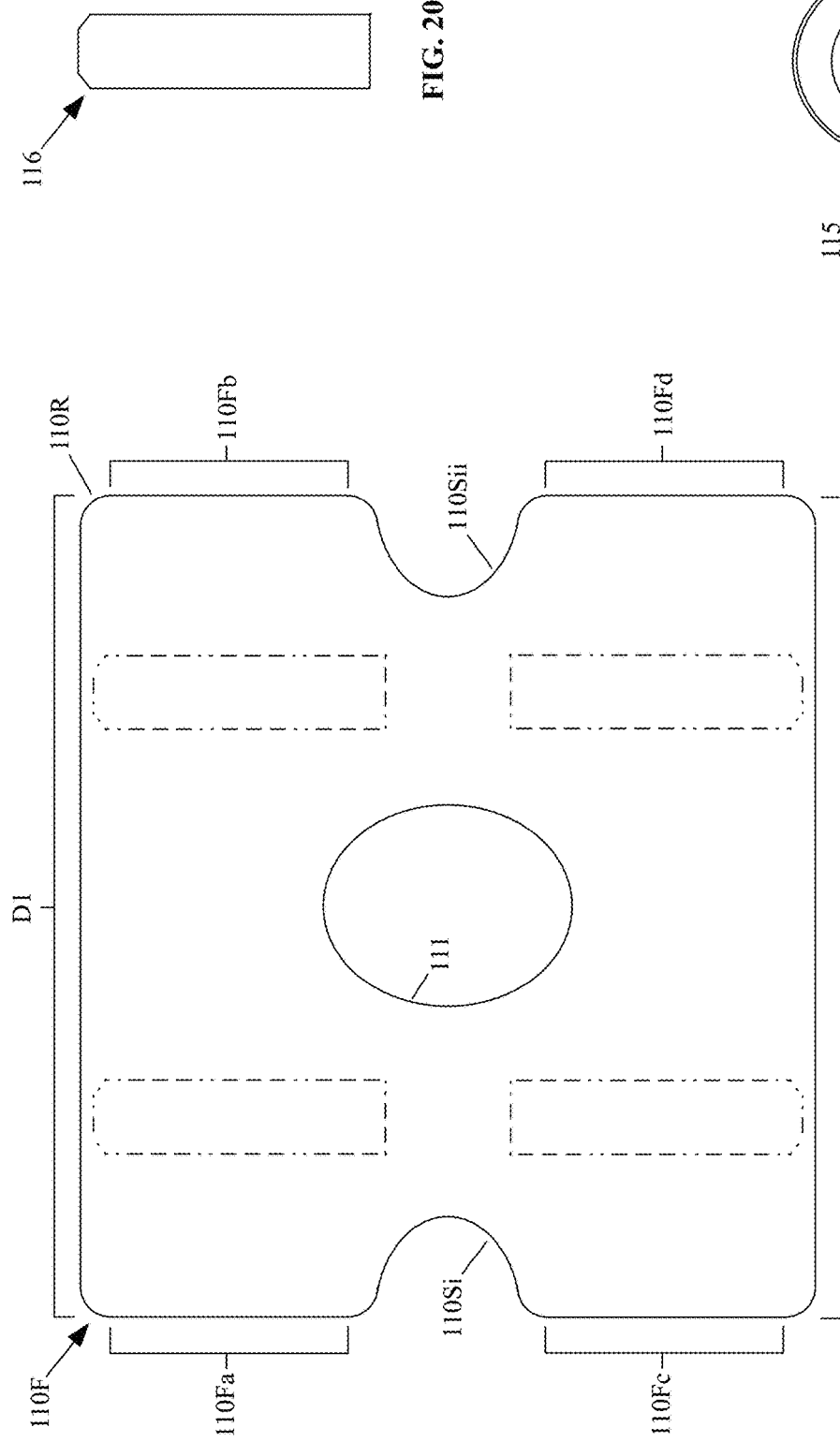
FIG. 18
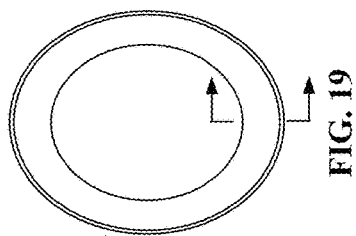
FIG. 19
FIG. 19A
FIG. 20

HINGED KNEE BRACE WITH DOUBLE UPPER STRAP ARRANGEMENT

CROSS REFERENCES TO RELATED APPLICATIONS

This application claims priority on U.S. Provisional Application Ser. No. 63/002,456, filed on Mar. 31, 2020, the disclosures of which are incorporated herein by reference.

FIELD OF THE INVENTION

This disclosure relates generally to orthotic devices, and more particularly to a knee orthosis with a double strap arrangement for securing the upper portion of the brace to the leg of the wearer above the knee joint to better prevent downward migration of the brace, which brace may also include a pair of polycentric hinges that are replaceable.

BACKGROUND OF THE INVENTION

Although there are many reasons for a person to wear a knee brace, the most common reason does not relate to an existing leg injury; conversely a knee brace is most commonly worn/utilized to protect the wearer's otherwise healthy knee from becoming injured. Many athletes and other people that may be at risk of a knee injury tend to wear a brace as a preventative measure—the knee brace helps prevent the wearer's knee joint from being forced into a position that would tend to cause an injury, including, but not limited to, twisting or overextending of the knee. In these cases, the brace is referred to as a functional brace, as it is utilized while the athlete's knee is still fully functional.

A knee brace that is not utilized as a preventative measure, is instead worn to address one or more issues relating to an injury. For example, a knee brace may be worn while recovering from an injury to help ensure complete healing and strengthening of the knee joint when it has not yet returned to its pre-injury status. Such a brace is referred to as a rehabilitative brace, and may serve to provide stability, support, and protection for the knee against an aggravating event that could result in greater injury to the knee than was initially suffered. The rehabilitative knee brace may also be worn to prevent or limit swelling that typically occurs with a knee injury. The standard "RICE" method for treating an injury calls for rest, ice, compression, and elevation. While the need for rest (i.e., putting little or no weight on the injured region) enables healing and prevents further injury, the steps of applying ice and compression to the injury and of elevating the injured limb are each directed to multiple aspects of the recovery that includes reducing and/or preventing further swelling of that region. Therefore, in compliance with the RICE method, a brace is therefore also worn to address the need for compression to reduce swelling of and around the injured knee joint.

Additionally, a knee brace is often worn to provide support/stability, to decrease pain, and enable greater functioning of a wearer's knee that may be afflicted from arthritis, whether osteoarthritis or inflammatory arthritis. Such knee brace wearers may find that any one of the different types of braces provide relief. For example, some patients with knee arthritis find benefits/relief from wearing a simple compressive wrap (i.e., a knee sleeve with an opening for the patella but without any hinge—see e.g., U.S. Pat. Nos.: 4,084,584 to Detty; and 5,139,477 to Peters). Some patients with knee arthritis find benefits/relief from wearing a patellofemoral brace that has pads or particular support surrounding the knee joint, which may prevent lateral subluxation (see e.g., U.S. Pat. Nos.: 4,607,628 to Dashefsky; 6,551,264 to Cawley; 7,083,586 to Simmons; and 9,113,998 to Romo). Other patients with knee arthritis find benefits/relief from wearing an unloader brace that is custom designed for the wearer and serves to shift stress away from the part of the knee with arthritis (i.e., shifting stress from the arthritic side to the other healthier side of the leg—see e.g., U.S. Pat. No. 9,610,188 to Walsh for a "VRB Cantilever-Based Unloader Brace Assembly"; and U.S. patent application Pub. No. 2018/0140505 (Barati) for "Vibratory Unloading Knee Brace for Knee Osteoarthritis"). Yet other patients with knee arthritis find benefits/relief from wearing a functional brace that has hinges (see e.g., U.S. Pat. Nos.: 4,372,298 to Lerman; 4,493,316 to Reed; 4,732,143 to Kausek; 4,986,264 to Miller; 5,358,469 to Patchel; 5,419,754 to Hutchins; 6,402,713 to Doyle; and 6,527,733 to Ceriani). It is noted that citing within this disclosure of any patents, published patent applications, and non-patent literature is not an admission as to any of those references constituting prior art with respect to the herein disclosed and claimed apparatus.

The wearer of a particular knee brace may experience several different problems, even where the brace is properly sized and suited for the person. One problem that persists is how to secure the brace to the leg, so that it does not tend to slide down. Most knee braces do not stay at the desired/optimal position at which they are initially secured, and distal knee brace migration can have a detrimental effect upon the efficacy of the support and stability that the brace is designed to provide. See e.g., Bracelayer Knee Stabilizing Compression Pants, "How to Stop Your Knee Brace from Slipping Down," Oct. 4, 2018; and Lower Extremity Review Magazine, "Minimizing the Effects of Knee Brace Migration," Shalmali Pal, Jun., 2012.

The herein disclosed apparatus provides improvements upon certain prior art knee braces, including, but not limited to, an improved upper strap securement arrangement that better prevents sliding down of the brace while being worn by the wearer.

OBJECTS OF THE INVENTION

It is an object of the invention to provide an improved knee orthosis.

It is another object of the invention to provide a pull-on knee brace that provides support for the knee joint and stability for the leg of the wearer.

It is a further object of the invention to provide a knee brace that prevents slipping of the brace downward while being worn by the wearer.

It is another object of the invention to provide a knee brace with a double upper strap arrangement that enhances securing of the brace to the leg of the wearer above the knee.

Further objects and advantages of the invention will become apparent from the following description and claims, and from the accompanying drawings.

It is noted that citing herein of any patents, published patent applications, and non-patent literature is not an admission as to any of those references constituting prior art with respect to the herein disclosed and/or claimed apparatus.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A knee brace embodiment as disclosed herein may include: an elastic sleeve, a first cinching strap, and a second cinching strap. The elastic sleeve may include: a first portion configured to encircle the leg of the wearer on a first side of the knee joint in proximity to the calf region, and apply a first level of compression; and a second portion being configured to encircle the leg of the wearer on a second side of the knee joint in proximity to the thigh region, and apply a second level of compression.

The first cinching strap may have a first end fixedly secured to the second portion of the elastic sleeve; and the second cinching strap may similarly have a first end fixedly secured to the second portion of the elastic sleeve. Additionally, the first cinching strap may be formed of a first length to permit the first cinching strap to wrap around the elastic sleeve at least one full circumferential loop in a first direction; and the second cinching strap may be formed of a second length to permit the second cinching strap to wrap around the elastic sleeve at least one full turn in a second direction, the second direction being opposite to the first direction. In one embodiment the first and second length of the first and second cinching straps may be slightly different, and in another embodiment, the two cinching straps may each have some excess length and may thus be formed such that the first length and the second length are the same length.

A first surface of the first cinching strap may be formed to include a loop material; and at least a portion of a second surface of the first cinching strap in proximity to a second end thereof may be formed to include a hook material configured to releasably secure to the loop material. Also, a first surface of the second cinching strap may be formed to include a loop material; and at least a portion of a second surface of the second cinching strap in proximity to a second end of the second cinching strap may be formed to include a hook material configured to releasably secure to the loop material of the first cinching strap and to the loop material of the second cinching strap.

The knee brace may also be formed to include: a first hinge socket formed on a first side of the first portion of the elastic sleeve; a first hinge socket formed on a first side of the second portion of the elastic sleeve; a second hinge socket formed on a second side of the first portion of the elastic sleeve; and a second hinge socket formed on a second side of the second portion of the elastic. Two of these sockets may accommodate a first polycentric hinge, whereby a first arm and a second aim of a first polycentric hinge are slidably received in the first hinge socket on the first side of the first portion of the elastic sleeve and the first hinge socket on the first side of the second portion of the elastic sleeve, respectively. Also, two of these sockets may accommodate a second polycentric hinge, whereby a first arm and a second arm of the second polycentric hinge are slidably received in the second hinge socket on the second side of the first portion of the elastic sleeve and the second hinge socket on the second side of the second portion of the elastic sleeve, respectively.

The hinge sockets may be formed in any suitable manner. However, the hinge sockets are preferably formed as follows.

The first hinge socket may be formed of: a first elongated flap of material having four sides, being fixedly secured on three of the four sides to a first side of the first portion of the elastic sleeve, to form an opening into the first hinge socket on the first side of the first portion of the elastic sleeve.

The second hinge socket may be formed of: a second flap of material having four sides, being fixedly secured on three of the four sides to a first side of the second portion of the elastic sleeve, to form an opening into the second hinge socket on the first side of the second portion of the elastic sleeve.

The third hinge socket may be formed of: a third flap of material having four sides, being fixedly secured on three of the four sides to a second side of the first portion of the elastic sleeve, to form an opening into the second hinge socket on the second side of the first portion of the elastic sleeve.

Lastly, the fourth hinge socket may be formed of: a fourth flap of material having four sides, being fixedly secured on three of the four sides to a second side of the second portion of the elastic sleeve, to form an opening into the second hinge socket on the second side of the second portion of the elastic sleeve.

Where the hinge sockets are formed as described, the first end of the first cinching strap may be fixedly secured to the second portion of the sleeve in proximity to first hinge socket on the first side of the second portion of the elastic sleeve; and the first end of the second cinching strap is fixedly secured to the second portion of the sleeve in proximity to first hinge socket on the second side of the second portion of the elastic sleeve. In addition, the first end of the first cinching strap may also be fixedly secured to second flap of material on the first side of the second portion of the elastic sleeve; and the first end of the second cinching strap may also be fixedly secured to the fourth flap of material on the second side of the second portion of the elastic sleeve.

For better securement of the cinching straps, at least an outer portion of the second flap of material may be formed of loop material, so that the hook material on the portion of the second surface of the first cinching strap may be releasably secured to the loop material on the outer portion of the second flap of material. Similarly, at least an outer portion of the fourth flap of material may be formed of loop material, so that the hook material on the portion of the second surface of the second cinching strap may be releasably secured to the loop material on the outer portion of the fourth flap of material.

The first cinching strap and second cinching strap are formed of a flexible material, which may also be an elastic material.

Similarly, each of the first, second, third, and fourth flaps of material are formed of a flexible material, which may also be an elastic material.

BRIEF DESCRIPTION OF THE DRAWINGS

The description of the various example embodiments is explained in conjunction with appended drawings, in which:

FIG. 1 is a front view of the improved knee brace disclosed herein;

FIG. 2 is a left side view of the knee brace of FIG. 1;

FIG. 3 is a right side view of the knee brace of FIG. 1;

FIG. 4 is a rear view of the knee brace of FIG. 1;

FIG. 18 is a flat pattern view of the elastic material that can be used to make the sleeve portion of the knee brace of FIG. 1;

FIG. 19 is a front view of a pad that may be sewn to the opening of the sleeve of FIG. 18 to support the patella while the brace is being worn; and FIG. 19A is a cross-sectional view through the pad of FIG. 19.

FIG. 20 illustrates a flap of material that may be secured to the elastic sleeve of the brace of FIG. 1 to form a socket to retain one arm of the polycentric hinge(s).

DETAILED DESCRIPTION OF THE INVENTION

Figure 5:
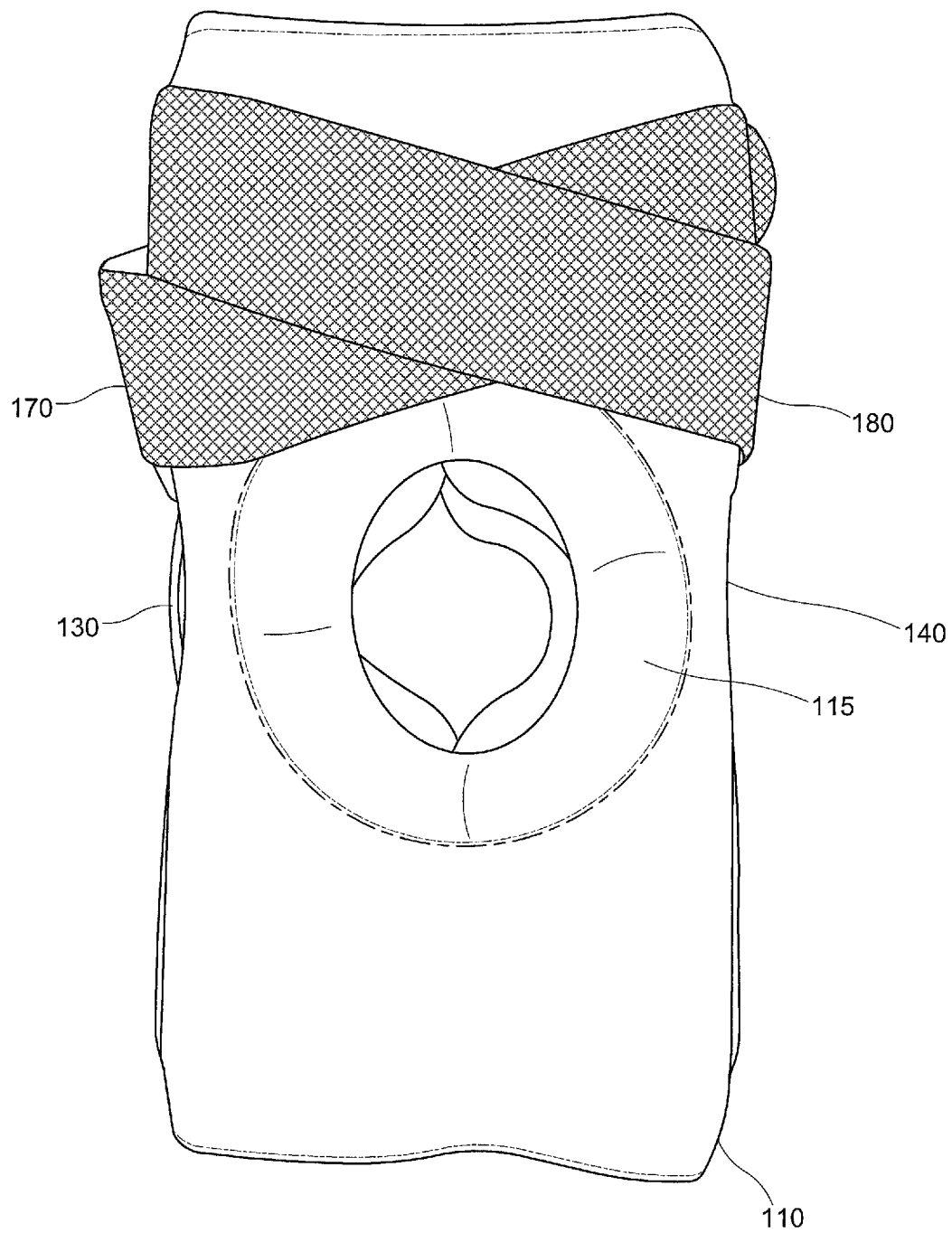
FIG. 5 is the front view of the knee brace as seen in FIG. 1, but shown enlarged.
Figure 6:
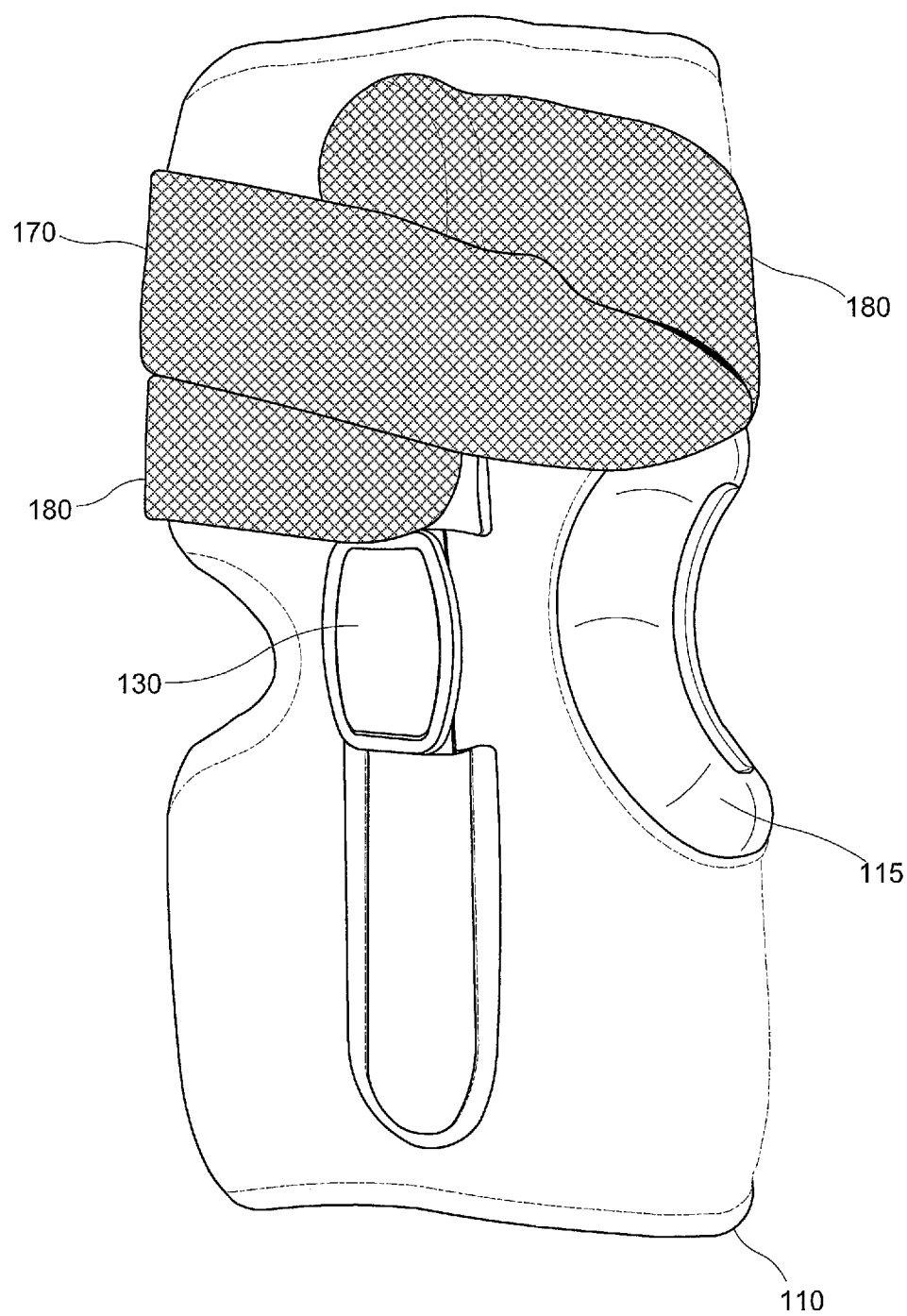
FIG. 6 is the left side view of the knee brace as seen in FIG. 2, but shown enlarged.
Figure 7:
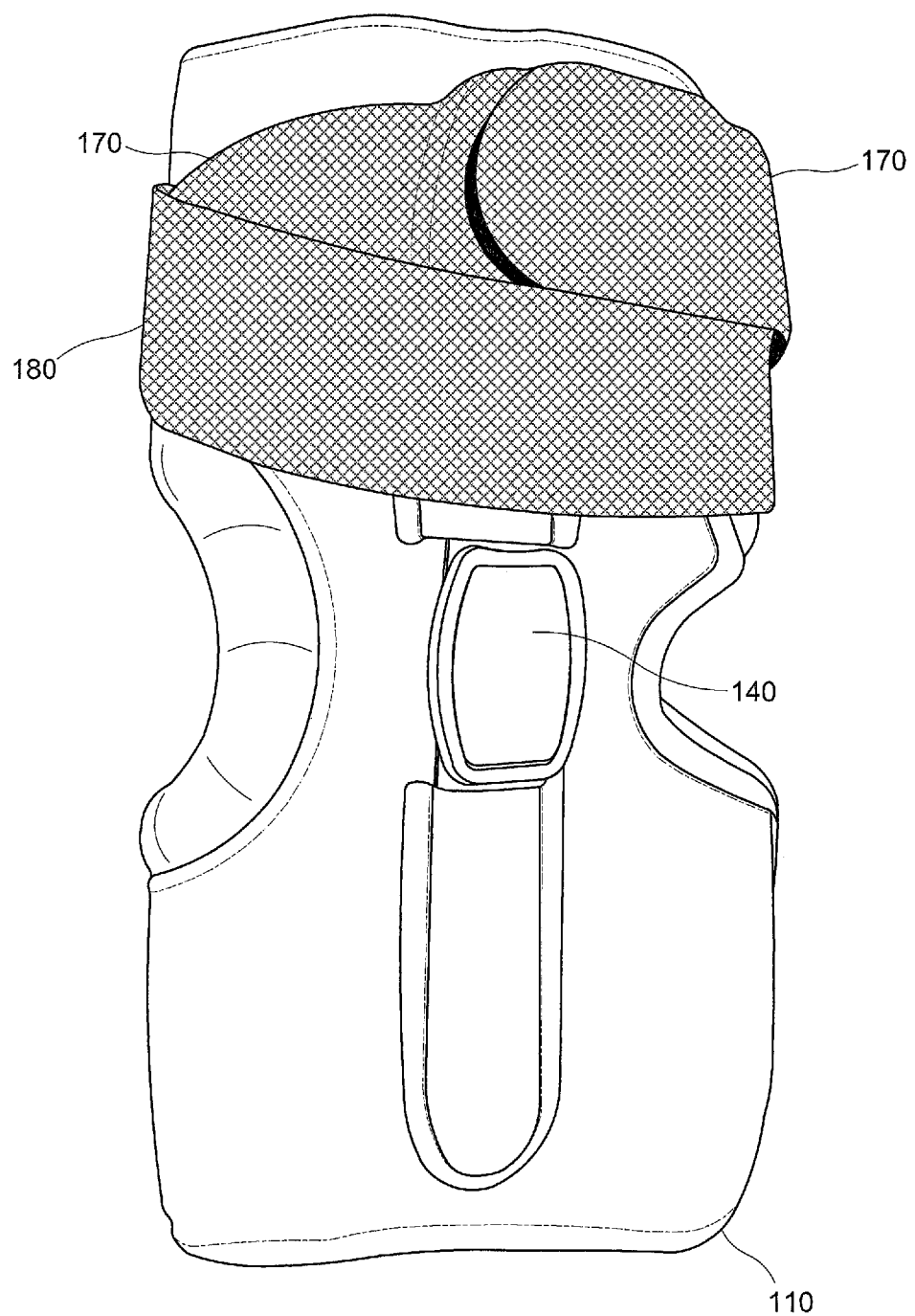
FIG. 7 is the right side view of the knee brace as seen in FIG. 3, but shown enlarged.
Figure 8:
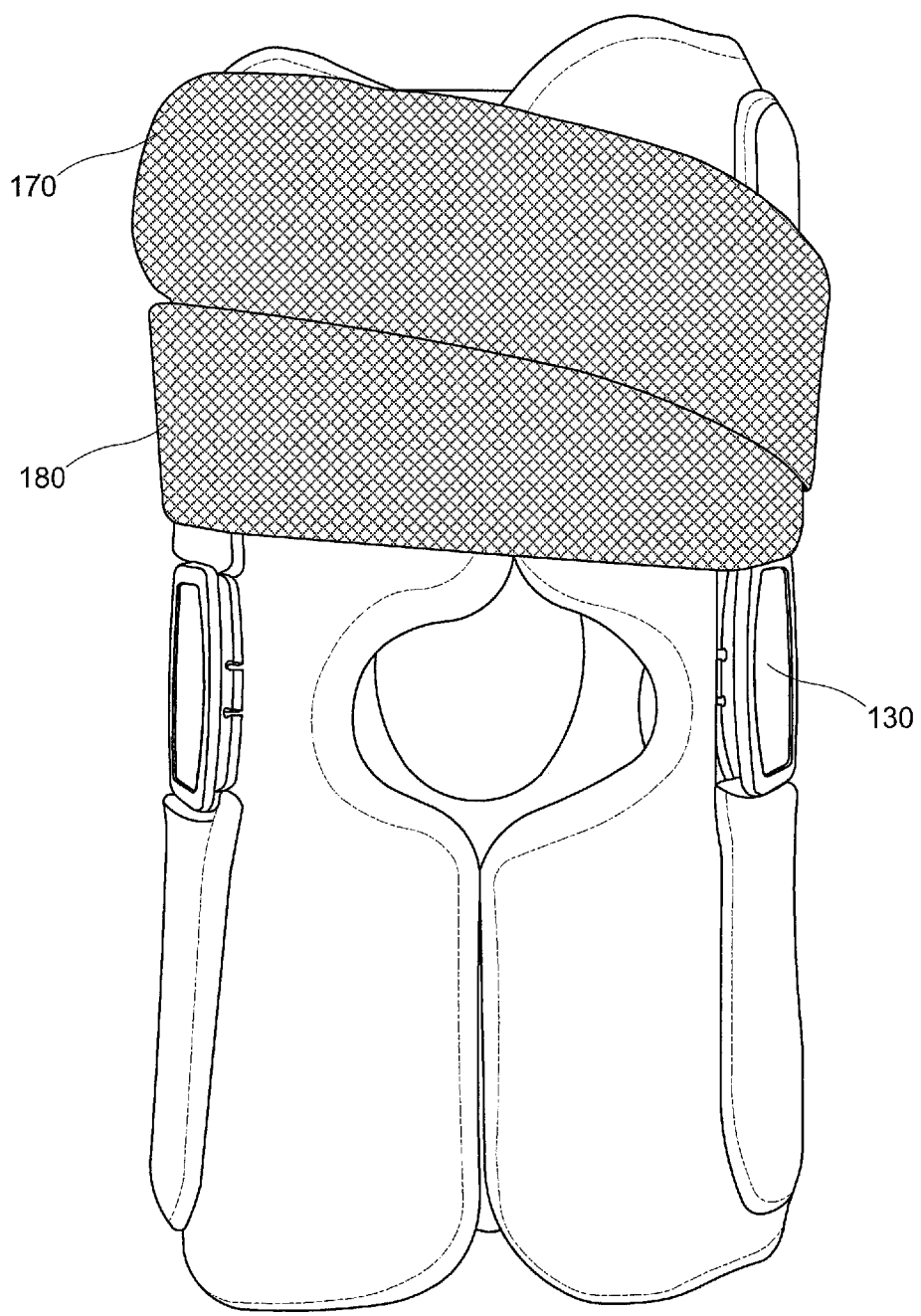
FIG. 8 is the rear view of the knee brace as seen in FIG. 4, but shown enlarged.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed and/or claimed apparatus/method.

Furthermore, any reference made throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of .0001 inches to .0003 inches, or an interference of .0003 inches to .0007 inches in another embodiment, or an interference of .0007 inches to .0010 inches in yet another embodiment, or a combination of such ranges.

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be .1360 inches for a free running fit; for a 0.5000 inch diameter shaft the opening may be 0.5156 inches for a close running fit and may be .5312 inches for a free running fit). Other clearance amounts are used for other clearance types.

The terms "rigid," and "flexible," and "resilient" may be used herein to distinguish characteristics of portions of certain features of the knee brace. Use of the term "rigid" indicates that the described element is devoid of flexibility such that it does not readily lose its overall shape when force is applied, and in fact it may break if an attempt to bend it is made with sufficient force. Use of the tern "flexible" indicates that the described element is capable of repeated bending such that it may be bent into different shapes and does not retain a general shape, but instead readily deforms when force is applied. Use of the term "resilient" indicates that the described element has such flexible features and also has a tendency to return to its initial general shape without permanent deformation once a force that causes such flexure is removed. Use of the term "semi-rigid" indicates that the described element may have some degree of flexibility or resiliency.

The knee brace disclosed herein may include either one or both of two different features, including a double upper strap arrangement to provide better support for maintaining the brace properly positioned on the wearer's leg; and/or a sleeve permitting replacement and interchangeability of a polycentric hinge thereby supported. For ease in describing the brace herein, a brace embodiment, i.e., brace 100, is described hereinafter that includes both features, with the understanding that both are not required in the other embodiments.

FIGS. 1-4 show front, left side, right side, and rear views of a knee brace embodiment-knee 100, which views are shown enlarged within FIGS. 5-8, respectively. The knee brace 100 may generally be formed of: an elastic sleeve 110, a first polycentric hinge 130, a second polycentric hinge 140, a left upper hinge socket 160L, a right upper hinge socket 160R, a left lower hinge socket 150L, a right lower hinge socket 150R, a left cinching strap 170, and a right cinching strap 180.

The elastic sleeve 110 utilized for the brace 100 may be formed of a single piece of the elastic material, or alternatively may be formed of several pieces of the elastic material that may be fixedly secured together, similar to the making of a garment of clothing. The elastic material utilized for the elastic sleeve 110 may be any suitable natural or synthetic material known in the art of orthotics, including, but not limited to, a neoprene material; a cloth material made of spandex, nylon, bamboo, etc.; blends thereof; the orthotic material shown by U.S. Pat. No. 5,735,807 to Cropper; etc.

Figure 10:
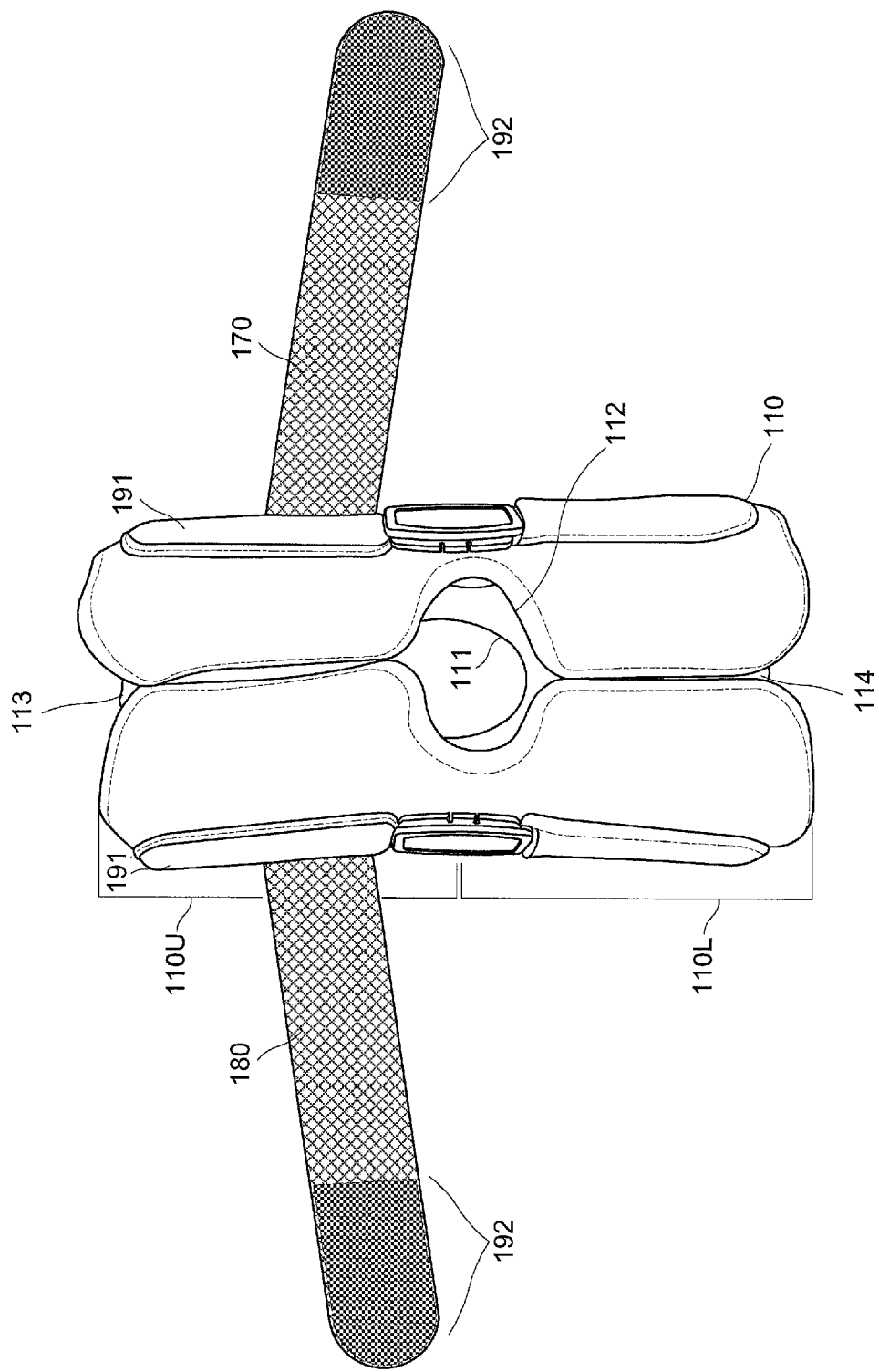
FIG. 10 is the rear view of the knee brace as seen in FIG. 9B, but shown with the end of the right upper securement strap detached from the hook/look material, and unwound from the rear side of the brace.
Figure 13:
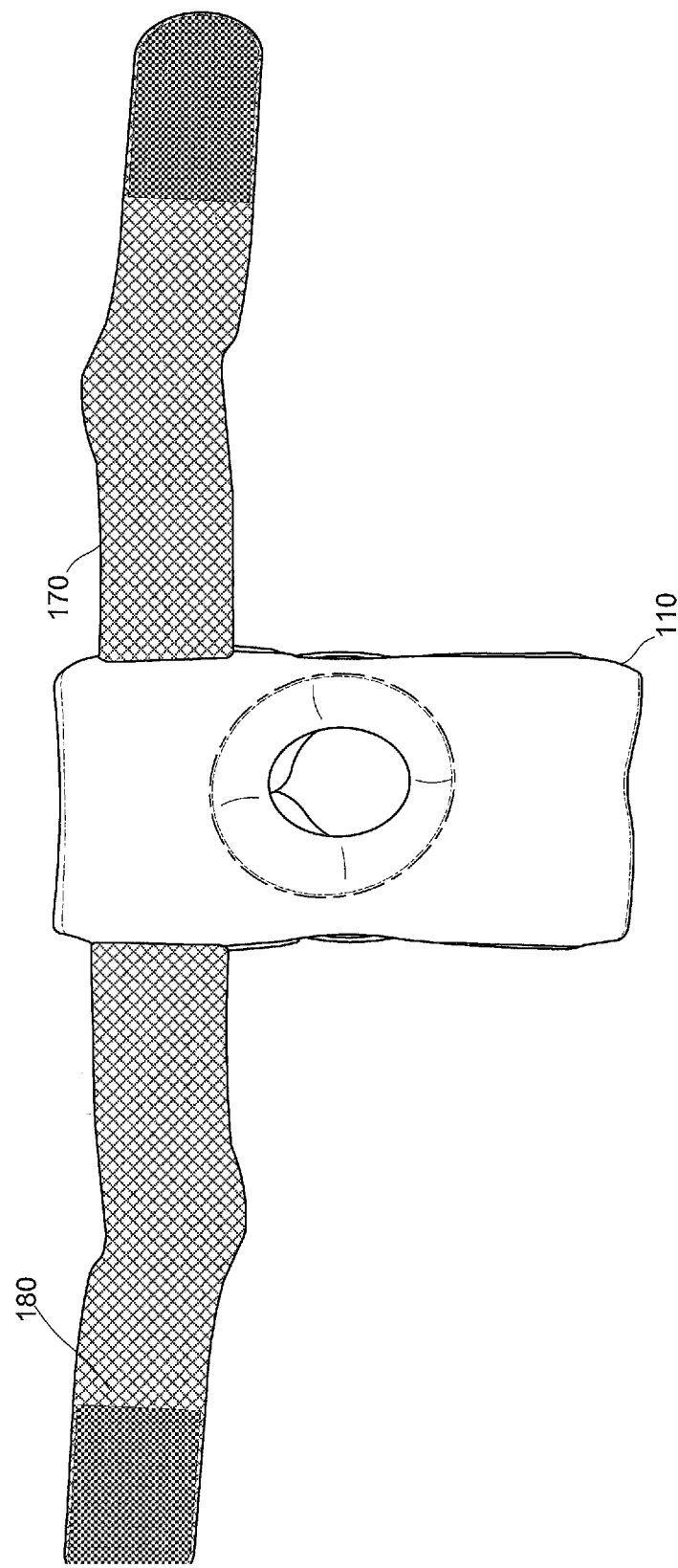
FIG. 13 is the front view of the knee brace as seen in FIG. 12, but shown with the end of the left upper securement strap unfolded and outstretched away from the left side of the brace.
Figure 14:
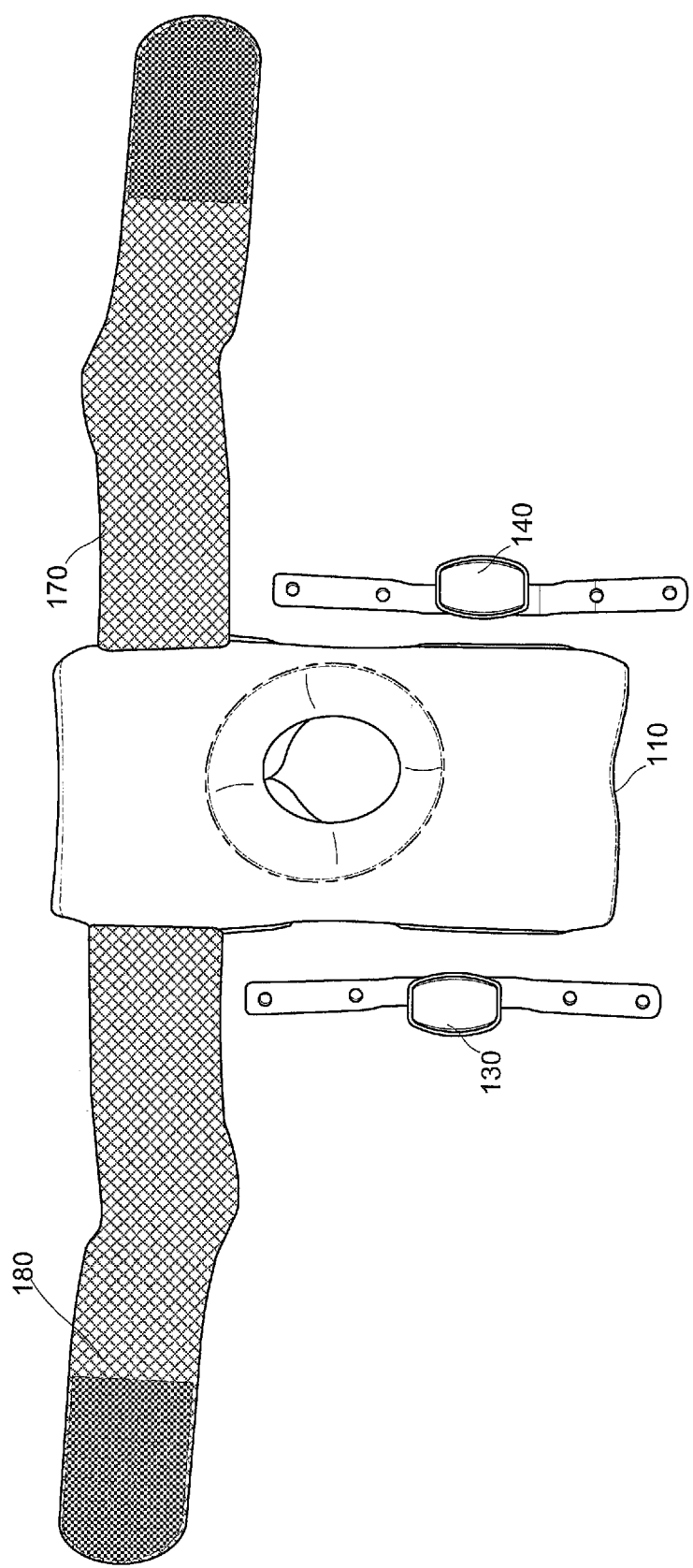
FIG. 14 is the front view of the knee brace as seen in FIG. 13, but shown with the left side hinge and the right side hinge each removed from the mounting sockets.

The elastic sleeve 110, as may be seen in FIG. 10 and FIG. 13, may be formed of one piece of elastic material that may be joined together, with an opening 111 formed in the front to accommodate the patella, and an opening 112 formed in the back to permit flexing of the knee joint without excessive gathering of the elastic material of the sleeve on the back of the leg when the leg is bent. The opening 111 and opening 112 may be formed in the flat pattern of material used for the sleeve 110 prior to assembling/stitching the sleeve together, or may be formed afterwards.

In the embodiment shown in the figures, the opening 111 may be formed in the flat pattern of the elastic material 110F (see FIG. 18) prior to joining of the ends, and which opening 111 may be circular in one embodiment, and in another embodiment, it may be slightly elliptical, with the major axis oriented in the vertical direction (i.e., oriented in the axial/lengthwise direction of the leg).

The opening 112 may be created by the particularly shaped periphery of the elastic material (i.e., having a scalloped shape 110Si on the left side and a scalloped shape 110Sii on the right side) that forms the opening 112 after joining of the ends of the fat piece of the elastic material 110F. The scalloped shape 110Si on the left side and the scalloped shape 110Sii on the right side may each be formed as half of an ellipse (or other elongated curved shape) with the major axis oriented in the horizontal direction, so that the opening 112 ultimately formed is elongated laterally to cover a significant portion, or even the entire portion, of the back of the leg of the wearer.

As seen in FIG. 18, the flat piece of material 110F used to form the elastic sleeve 110 may be generally rectangular, except for the scalloped shapes 110Si/110Sii and the rounded corners 110R. The sleeve 110 may be formed by having the ends 110Fa and 110Fb be fixedly secured to each other (e.g., by stitching) at 113 to form the upper portion 110U (see FIG. 10), and by having the ends 110Fc and 110Fd be wrapped around and be fixedly secured to each other at 114 to form the lower sleeve portion 110L. The lower sleeve portion 110L may be sized and shaped to encircle the wearer's leg at and/or below the knee (e.g., to encircle at least portions of the mid-calf and/or the upper calf muscle of the wearer's leg) and apply a first level of compression thereto. The upper sleeve portion 110U may be sized and shaped to encircle the wearer's leg at and/or above the knee (e.g., to encircle at least portions of the thigh of the wearer's leg), and apply a second level of compression thereto. In one embodiment, the sleeve portions may be particularly sized for the wearer's leg size/shape to apply a second level of compression to the thigh region that is higher than the first level of compression, to better maintain the upper part of the sleeve around the thigh of the wearer, to prevent downward migration, and in another embodiment the second level of compression may be about the same as the first level of compression. As the thigh area of the leg tends to be larger than the calf area, the distance D1 between the ends 110Fa and 110Fb shown for the flat pattern 110F in FIG. 18 may be larger than the distance D2 between the ends 110Fc and 110Fd. Also, at least the ends 110Fa and 110Fb may be angled slightly with respect to each other to form a slight trapezoidal shape for that portion of the flat pattern 110F, thereby creating a slight conical shape for the upper sleeve portion 110U. It is noted that rather than stocking an assortment of different sizes and shapes for the brace 100, these and other aspects of the elastic sleeve 110 may be customize for each person, according to the measurements of the geometry of the wearer's lower leg and the measurements of the upper leg of the wearer.

Secured (e.g., sewn) to the opening 111 of the elastic sleeve 110 may be an annular patellofemoral pad 115 (FIGS. 19 and 19A), which may be foam filled, and which may surround and provide support to the patella portion of the knee joint, to prevent lateral subluxation while the brace 100 is being worn. The pad 115 may have a casing, which may be elastic, and which may have a small lateral extension 115E protruding radially, to provide a convenient surface for securement to the region of the elastic sleeve 110 proximate to the opening 111.

Figure 21:
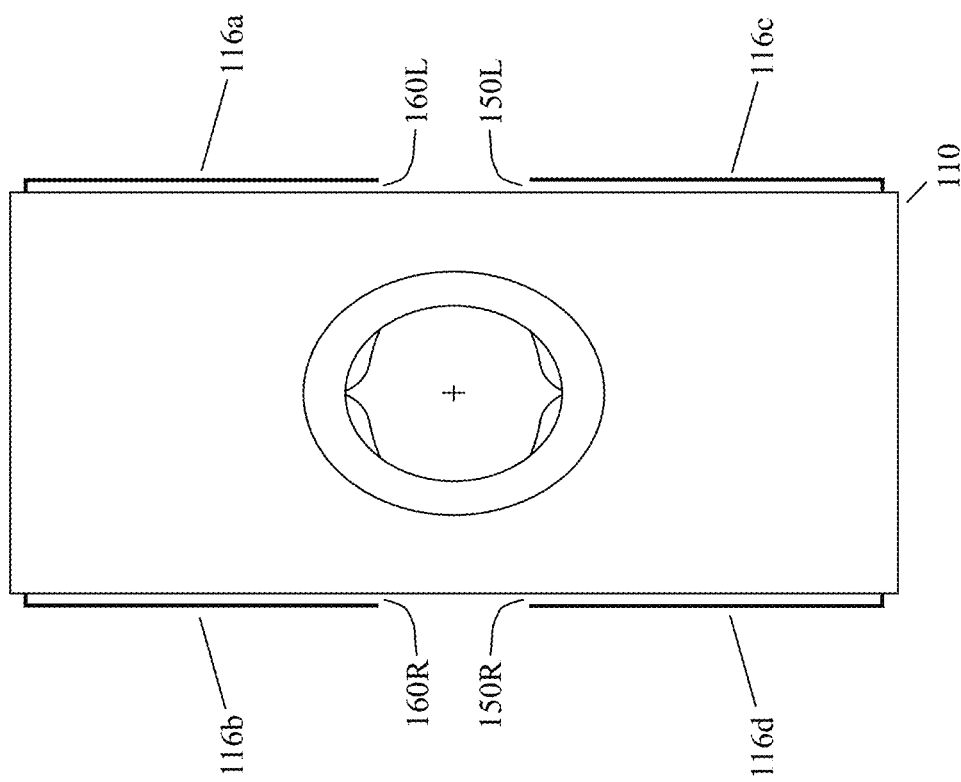
FIG. 21 shows the elastic material of FIG. 19 after having its ends secured to form the sleeve of the brace of FIG. 1, and shown with the patella support pad secured thereto, and with the four flaps of material secured thereto to form the hinge support sockets for the two polycentric hinges.

To retain and support the respective upper and lower arms of the polycentric hinges 130/140, the sleeve 110 may have a corresponding flap of material 116 (FIG. 20) be secured at each of the appropriate locations (i.e., the outlines shown using phantom lines in FIG. 18). The flap of material 116 may be elongated and be shaped to correspond to the shape of the arm(s) of the hinges, with a little excess. The flap of material may be secured to the elastic sleeve 110 along a substantial extent of its periphery (e.g., three of four sides where a rectangular shaped flap material is utilized), leaving only a portion unsecured (i.e., unstitched) to create an opening on one end thereof into the socket (see FIG. 21), through which the end of the arm of the hinge may be received. Four flaps of material (i.e., 116a, 116b, 116c, and 116d) may be used to form the four hinge sockets—the left upper hinge socket 160L, the right upper hinge socket 160R, the left lower hinge socket 150L, and the right lower hinge socket 150R.

Figure 15:
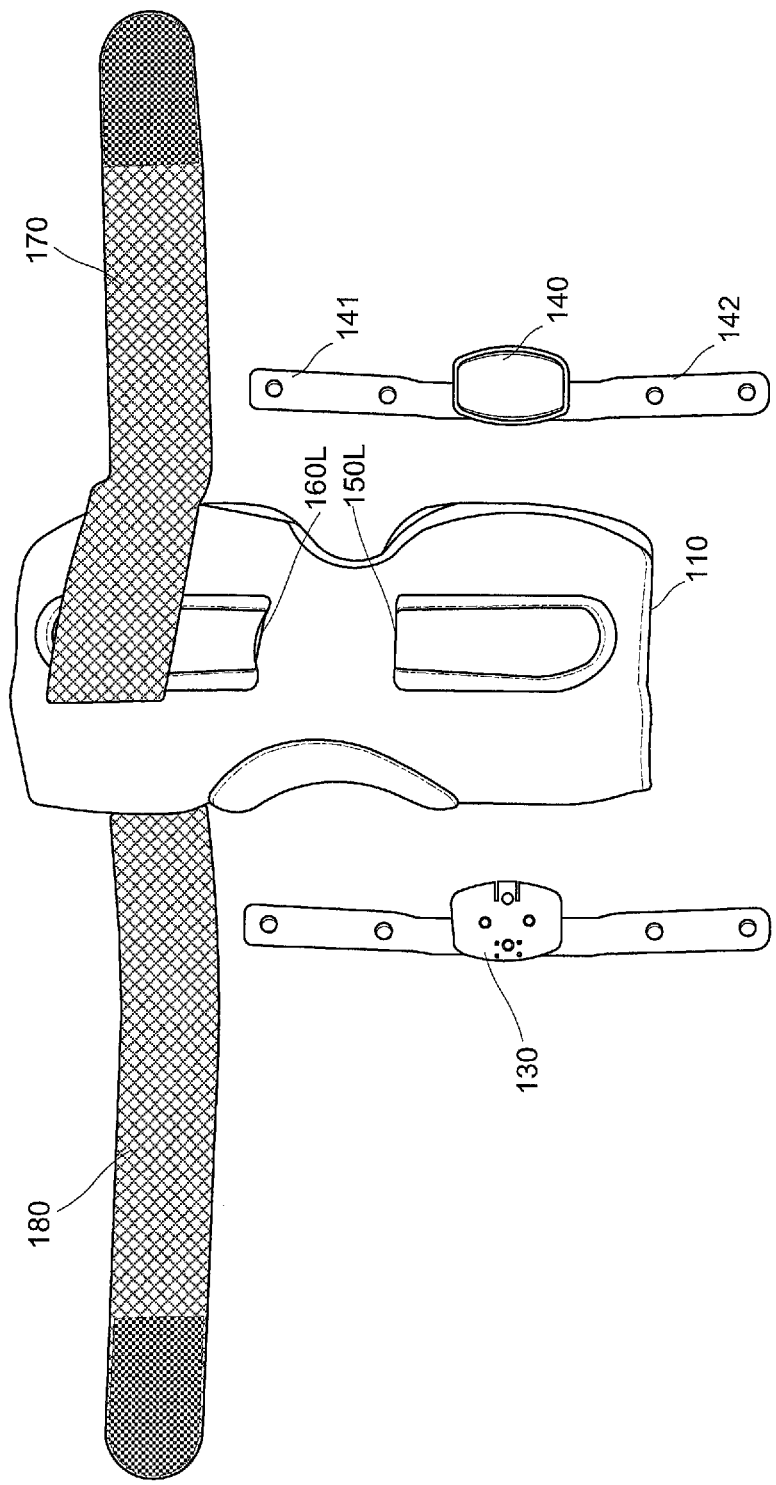
FIG. 15 is a left side view of the knee brace as arranged in FIG. 14, showing the upper socket and lower socket on the left side prior to receiving the arms of the corresponding polycentric hinge.
Figure 16:
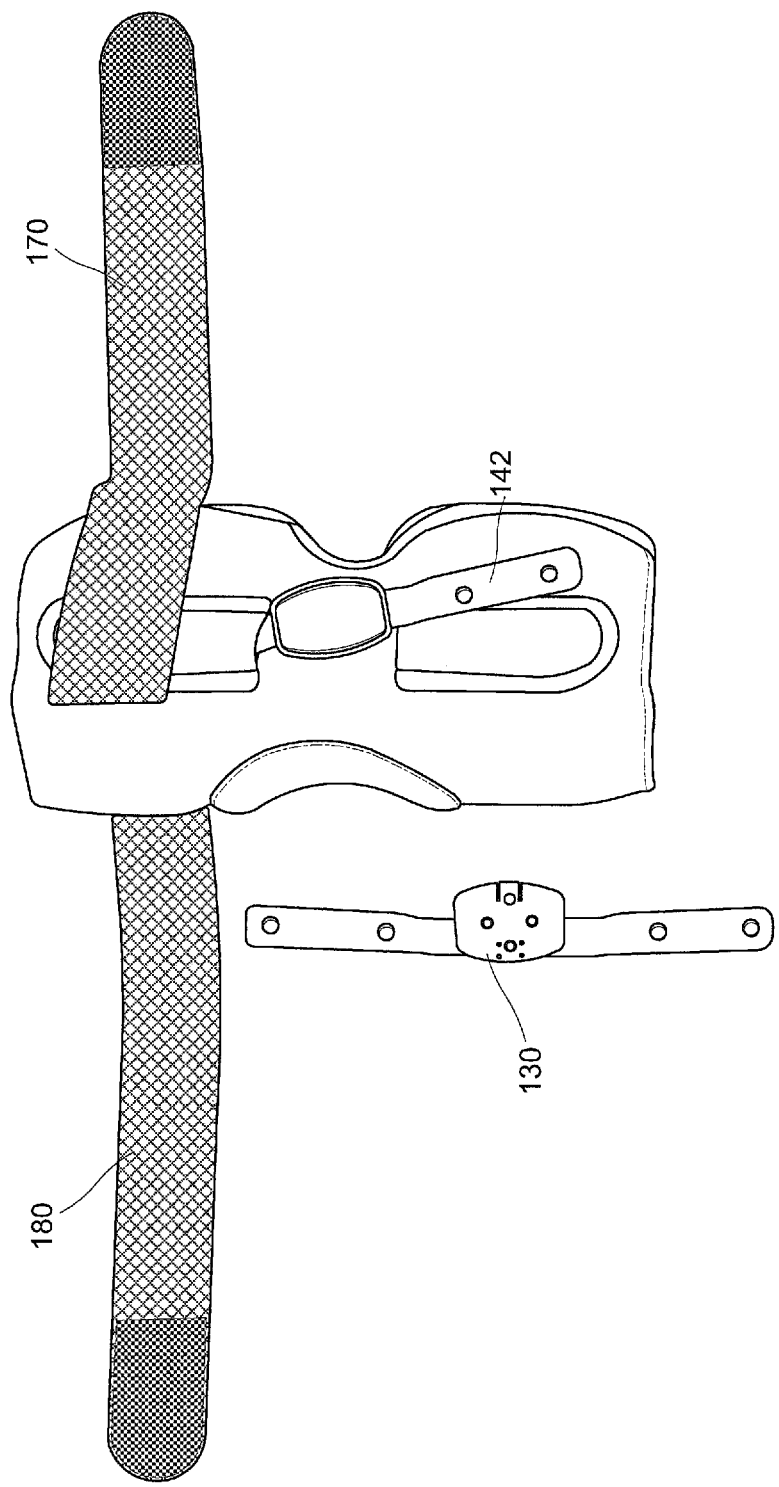
FIG. 16 is the left side view of the knee brace as shown in FIG. 15, but shown after the upper arm of the corresponding polycentric hinge has been inserted into the upper socket.
Figure 16A:
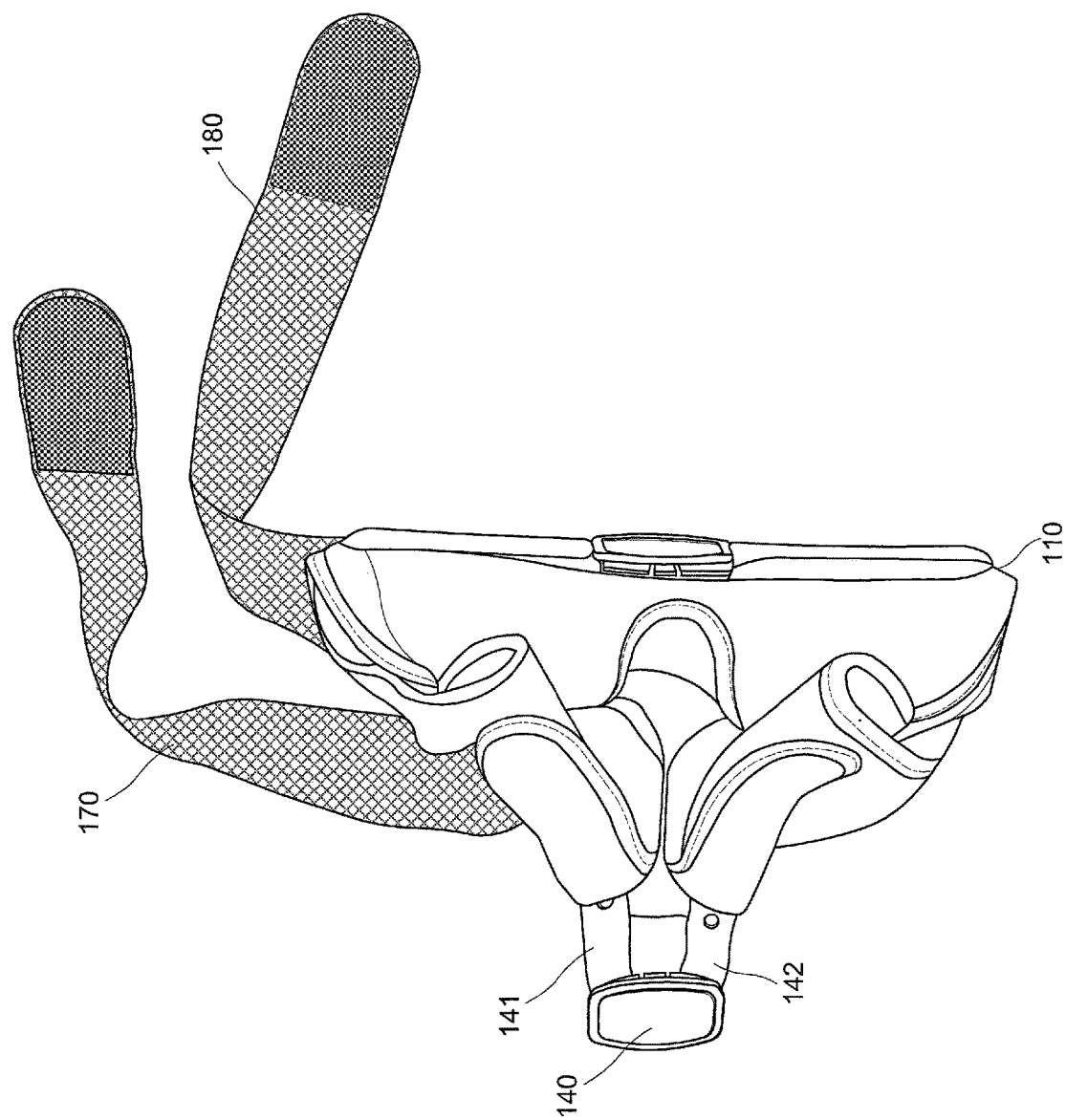
FIG. 16A is the left side view of the knee brace as shown in FIG. 16, but shown after the elastic sleeve of the brace has been deformed to place the upper socket into relative alignment with the lower socket, to permit insertion of at least a portion of the lower arm of the polycentric hinge into the lower socket.
Figure 17:
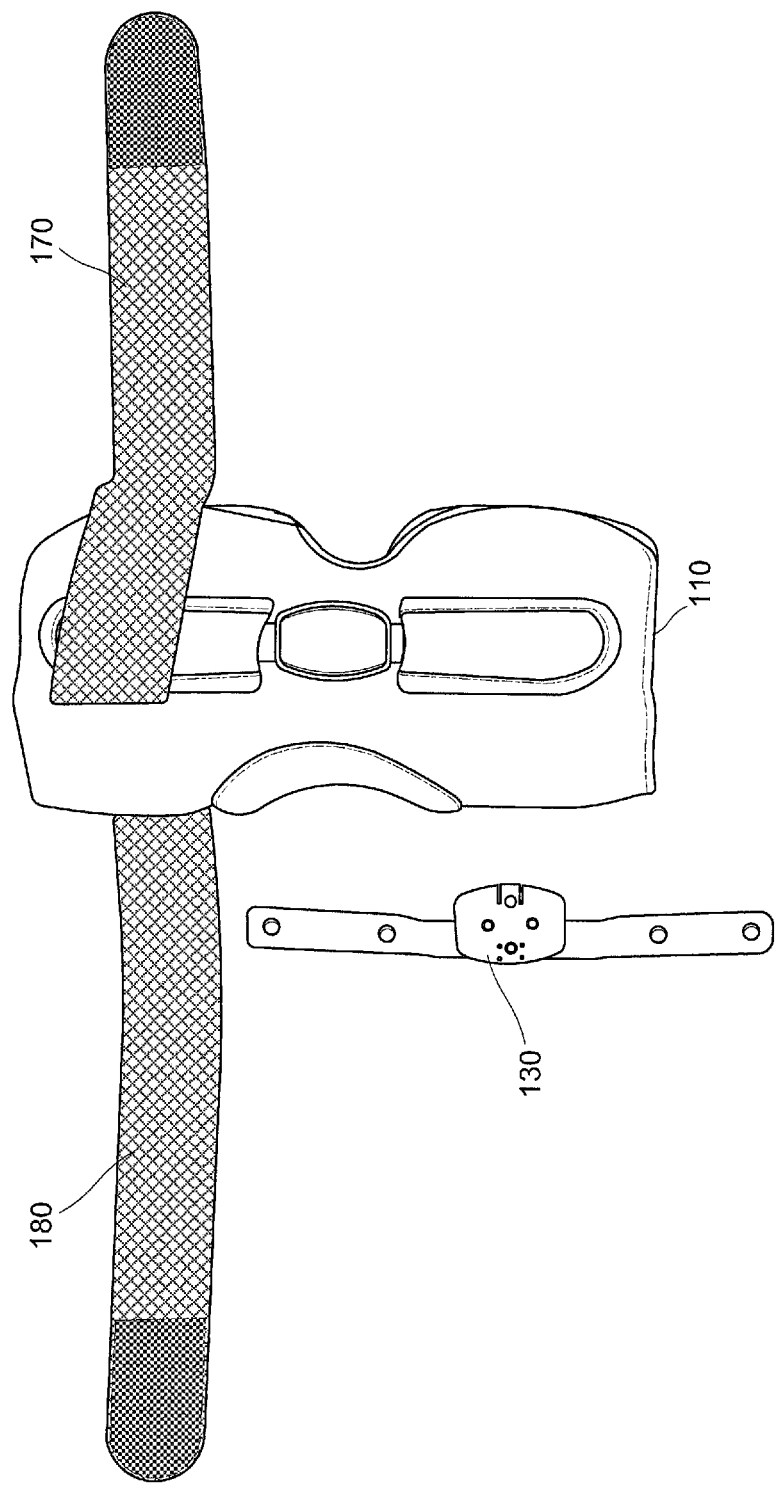
FIG. 17 is the left side view of the knee brace as shown in FIG. 16A, but shown after the upper and lower anus of the polycentric hinge have been fully inserted into the upper and lower sockets, and the elastic sleeve of the brace has been restored to its typical un-deformed position.

FIG. 15 shows the left upper hinge socket 160L and left lower hinge socket 150L on the left side of the knee brace 100, being shown prior to receiving the arms 141/142 of the polycentric hinge 140 therein. FIG. 16 illustrates the left side of the knee brace 100 as shown in FIG. 15, but is shown after the upper arm 141 of the hinge 140 has been inserted into the upper hinge socket 160L. FIG. 16A shows the flexible elastic sleeve 110 of the brace 100 after being deformed to place the axial direction of the upper hinge socket 160L into relative alignment with the axial direction of the lower hinge socket 150L, to permit insertion of at least a substantial portion of the lower arm 142 of the hinge 140 into the lower hinge socket 150L. FIG. 17 illustrates the left side of the knee brace 100 as shown in FIG. 16A, but is shown after the upper and lower arms 141/142 of the polycentric hinge 140 have been fully inserted into the upper hinge socket 160L and lower hinge socket 150L, and the elastic sleeve 110 of the brace has been restored to its typical un-deformed position along with the arms 141/142. Therefore, the four flaps of material (i.e., 116a, 116b, 116c, and 116d) are preferably formed of at least a flexible material, and may more preferably be formed of an elastic material, which in one embodiment may be the same elastic material used for the sleeve 110.

The left cinching strap 170 and right cinching strap 180 may each be formed of a flexible material. In one embodiment the straps 170 and 180 may be flexible but generally inelastic; and in another embodiment, the straps may be flexible and may also exhibit at least some degree of elasticity, which may help to tension each strap around the thigh of the wearer's leg to better secure the brace 100 to the wearer.

A first end of the left cinching strap 170 may be fixedly secured (e.g., by stitching) to the upper portion 110U of the sleeve 110 at a position in proximity to the left upper hinge socket 160L, as seen in FIG. 13. Similarly, a first end of the right cinching strap 180 may be fixedly secured to the upper portion 110U of the sleeve 110 at a position in proximity to the right upper hinge socket 160R. In one embodiment, the cinching straps 170/180 may be secured adjacent to the flap of material that forms the respective hinge socket; and in another embodiment, the cinching straps 170/180 may be secured beneath the flap of material that forms the respective hinge socket.

The second end of each of the left cinching strap 170 and right cinching strap 180 may be formed to include either a piece of hook type material, or the corresponding loop type material to which the hook type material can be releasably attached—which hook and loop materials are descriptive names for such materials that are sold under the trademark VELCRO ®. Also, the exterior sides of each of the four flaps of material (i.e., flaps 116a, 116b, 116c, and 116d) used to create the sockets may be formed to include the other of those hook type and loop type materials that are used on the straps. For example, as seen in FIG. 10, the exterior side of each of the four flaps of material (i.e., 116a, 116b, 116c, and 116d) may be formed to include the loop type material 191, and the first ends of each of the left cinching strap 170 and right cinching strap 180 may be formed to include the hook type material 192.

Therefore, each of the left cinching strap 170 and right cinching strap 180 may be formed of a length that permits them to be respectively wrapped around the sleeve 110 at least one full circumferential loop in opposite directions, such that the hook type material 192 at each of the first ends of the straps may be respectively secured to the loop type material 191 of the flaps forming the upper left and right hinge sockets 160L and 160R.

Figure 9A:
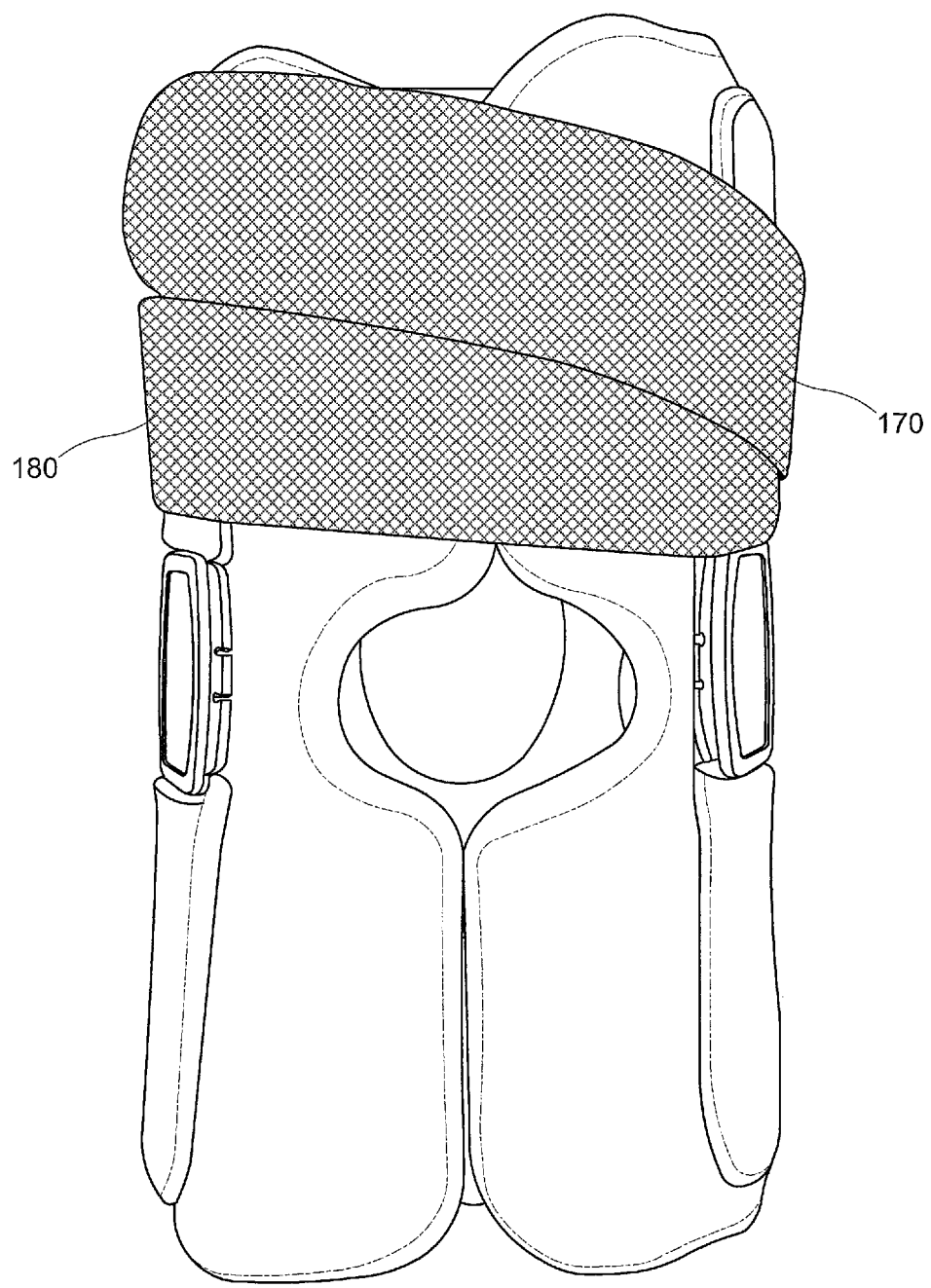
FIG. 9A is the rear view of FIG. 8, shown side by side with FIG. 9B.
Figure 9B:
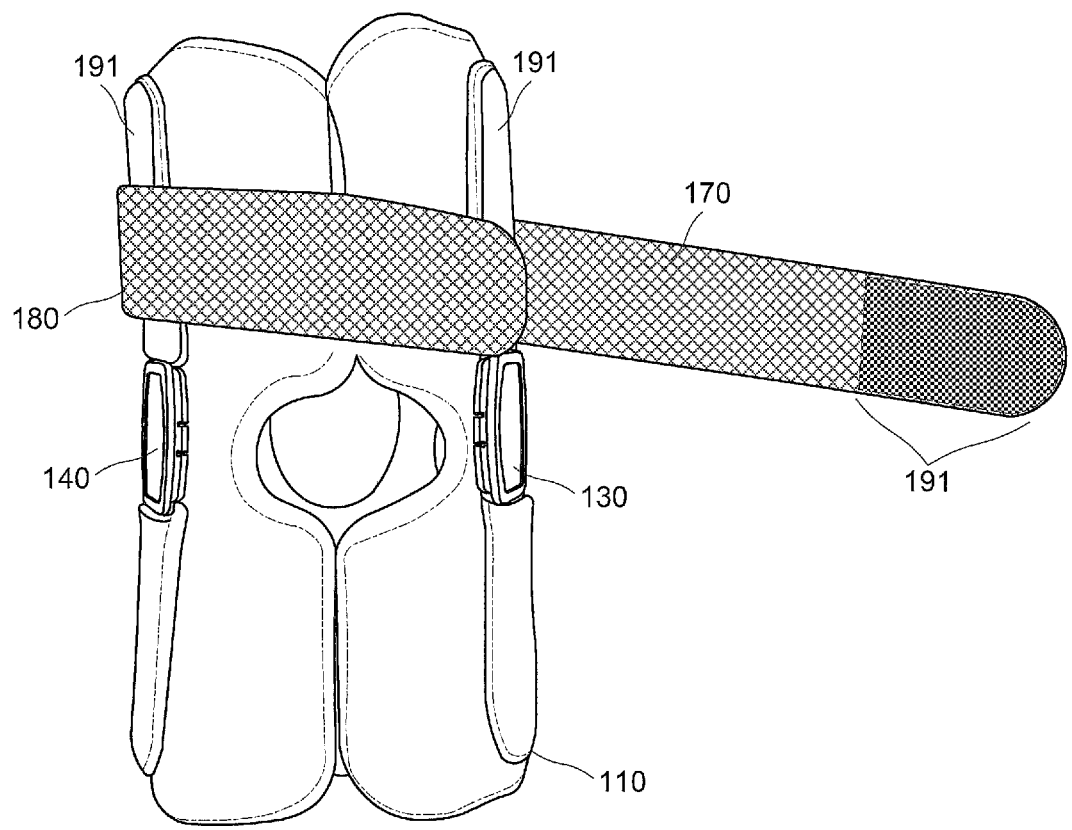
FIG. 9B is the rear view of the knee brace as seen in FIG. 9, but shown with the end of the left upper securement strap detached from the hook/look material, and unwound from the rear side of the brace.
Figure 11:
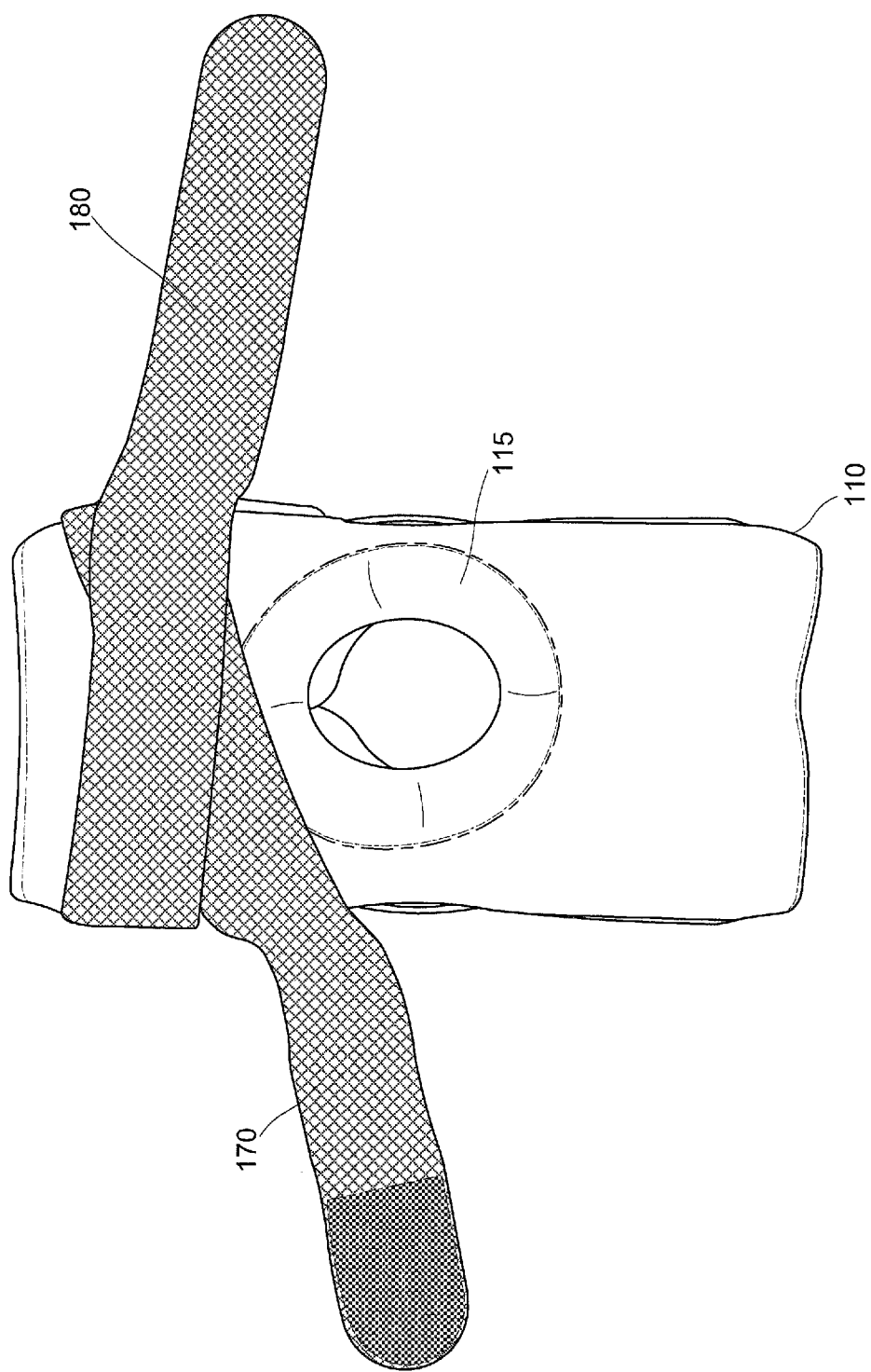
FIG. 11 is the front view of the knee brace as arranged in FIG. 10.
Figure 12:
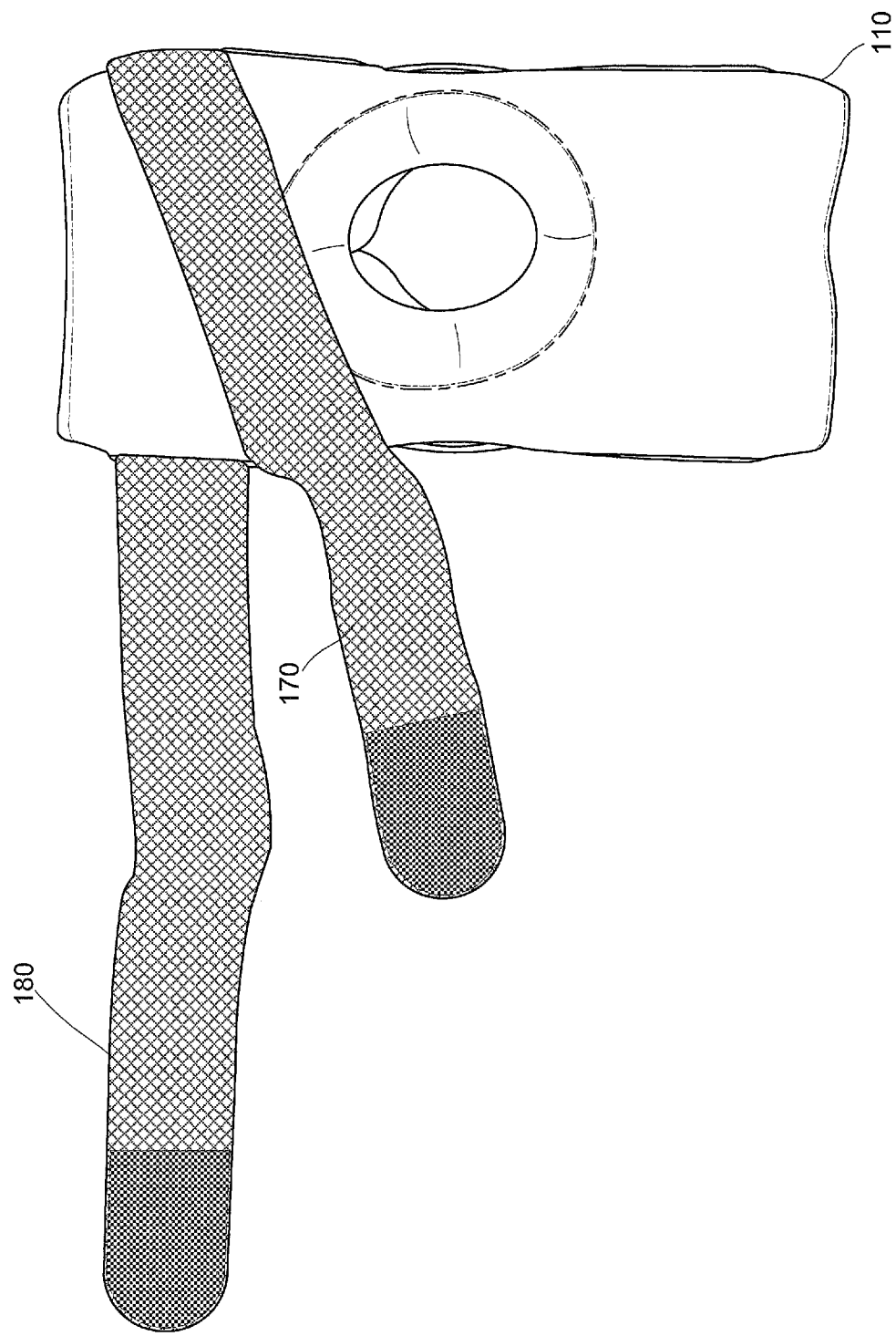
FIG. 12 is the front view of the knee brace as seen in FIG. 11, but shown with the end of the right upper securement strap unfolded and outstretched away from the right side of the brace.

FIG. 13 shows the left cinching strap 170 and right cinching strap 180 outstretched from the sleeve 110. Once the sleeve has been properly positioned on the leg and knee of the wearer, one of the two cinching straps, e.g., strap 170 as seen in FIG. 12, may be pulled/wrapped around the sleeve 110 (e.g., across the front of the sleeve). The other cinching strap (i.e., strap 180) may also then be pulled around the sleeve 110 (e.g., across the front of the sleeve), as shown in FIG. 11. The two cinching straps being initially wrapped/wound around the front of the sleeve, as shown in FIG. 11, would appear from the rear as seen in FIG. 10. Therefore, in comparing FIGS. 10 and FIG. 9B, it may be seen that subsequently, one of the two cinching straps (e.g., strap 180) may be wrapped across the back of the sleeve 110 and have the hook type material 192 on its end be releasably secured to the loop type material 191 on the flap on the right side of the sleeve 110 (FIG. 9B). Lastly, as may be seen in comparing FIG. 9B and FIG. 9A, the other strap—cinching strap 170—may then be wrapped around the back of the sleeve 110 and have the hook type material 192 on its end be releasably secured to the loop type material 191 on the flap on the left side of the sleeve 110, as seen in FIG. 9A.

It should be understood that the above description for securement of the cinching straps 170 and 180 is exemplary, and that the order of wrapping and securement may be changed from the described sequence.

To enable suitable tensioning of the cinching straps while still permitting releasable attachment of the hook type material 192 on its ends to the loop type material 191 on the respective flaps, for different sized thighs of different wearers, the length of the hook type material 192 may at least be in the range of one-quarter to one-third of the overall length of the strap (see FIG. 10). Other lengths for the cinching straps and for the hook type material 192 on its ends may alternatively be used. For example, the length of the cinching straps may permit them to be wrapped around the thigh of the wearer one and a half times instead of only one time, permitting securement of its end to the flap on the opposite side; and the length of the hook type material 192 may instead be in the range of one-third to one-half of the overall length of the strap.

While illustrative implementations of one or more embodiments of the disclosed brace are provided hereinabove, those skilled in the art and having the benefit of the present disclosure will appreciate that further embodiments may be implemented with various changes within the scope of the disclosed brace. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A knee brace comprising:
   an elastic sleeve; said elastic sleeve comprising: a first portion being configured to encircle a leg of a wearer on a first side of a knee joint in proximity to a calf region, and to apply a first level of compression; and a second portion being configured to encircle the leg of the wearer on a second side of the knee joint in proximity to a thigh region, and to apply a second level of compression;
   a first cinching strap, said first cinching strap having a first end fixedly secured to a first side of said second portion of said elastic sleeve, and being fixedly secured proximate to a top of said elastic sleeve;
   a second cinching strap, said second cinching strap having a first end fixedly secured to a second side of said second portion of said elastic sleeve, and being fixedly secured proximate to said top of said elastic sleeve, wherein said attachment of said first cinching strap and said attachment of said second cinching strap are symmetric with respect to a midplane of said elastic sleeve;
   wherein said first cinching strap is formed of a first length, said first length configured for said first cinching strap to wrap in a first direction around said elastic sleeve at least one full circumferential loop;
   wherein said second cinching strap is formed of a second length, said second length configured for said second cinching strap to wrap in a second direction around said elastic sleeve at least one full turn;
   wherein said second direction is opposite to said first direction;
   wherein a first surface of said first cinching strap comprises a loop material; and wherein at least a portion of a second surface of said first cinching strap in proximity to a second end thereof comprises a hook material configured to releasably secure to said loop material;
   wherein a first surface of said second cinching strap comprises a loop material; and wherein at least a portion of a second surface of said second cinching strap in proximity to a second end of said second cinching strap comprises a hook material configured to releasably secure to one or more of said loop material of said first cinching strap and said loop material of said second cinching strap;
   wherein said first length of said first cinching strap is configured to wrap said one full circumferential loop in a first downward helical direction around said second portion of said elastic sleeve;
   wherein said second length of said second cinching strap is configured to wrap said one full turn in a second downward helical direction around said second portion of said elastic sleeve; and
   wherein said first cinching strap and said second cinching strap crisscross as a result of said wrap in said first downward helical direction and said wrap in said second downward helical direction; and
   wherein said first cinching strap and said second cinching strap are thereby configured to prevent sliding down of the brace while being worn on the leg of the wearer.

2. The knee brace according to claim 1, further comprising:
   a first hinge socket, said first hinge socket formed on a first side of said first portion of said elastic sleeve;
   a second hinge socket, said second hinge socket formed on a first side of said second portion of said elastic sleeve;
   a third hinge socket, said third hinge socket formed on a second side of said first portion of said elastic sleeve;
   a fourth hinge socket, said fourth hinge socket formed on a second side of said second portion of said elastic sleeve;
   a first polycentric hinge, said first polycentric hinge comprising: a first arm and a second arm, said first arm and said second arm configured to be slidably received in said first hinge socket and said second hinge socket, respectively; and
   a second polycentric hinge, said second polycentric hinge comprising: a first arm and a second arm, said first arm and said second arm of said second polycentric hinge configured to be slidably received in said third hinge socket and said fourth hinge socket, respectively.

3. The knee brace according to claim 2,
   wherein said first hinge socket comprises: a first flap of material, said first flap of material having four sides, being fixedly secured on three of said four sides to said first side of said first portion of said elastic sleeve, to form an opening into said first hinge socket on said first side of said first portion of said elastic sleeve;
   wherein said second hinge socket comprises: a second flap of material, said second flap of material having four sides, being fixedly secured on three of said four sides of said second flap of material to said first side of said second portion of said elastic sleeve, to form an opening into said second hinge socket on said first side of said second portion of said elastic sleeve;
   wherein said third hinge socket comprises: a third flap of material, said third flap having four sides, being fixedly secured on three of said four sides of said third flap to said second side of said first portion of said elastic sleeve, to form an opening into said third hinge socket on said second side of said first portion of said elastic sleeve; and
   wherein said fourth hinge socket comprises: a fourth flap of material, said fourth flap having four sides, being fixedly secured on three of said four sides of said fourth flap to said second side of said second portion of said elastic sleeve, to form an opening into said fourth hinge socket on said second side of said second portion of said elastic sleeve.

4. The knee brace according to claim 3,
   wherein said first end of said first cinching strap is fixedly secured to said second portion of said sleeve in proximity to said first hinge socket on said first side of said second portion of said elastic sleeve; and
   wherein said first end of said second cinching strap is fixedly secured to said second portion of said sleeve in proximity to said fourth hinge socket on said second side of said second portion of said elastic sleeve.

5. The knee brace according to claim 4,
   wherein said first end of said first cinching strap is also fixedly secured to said second flap of material on said first side of said second portion of said elastic sleeve; and wherein said first end of said second cinching strap is fixedly secured to said fourth flap of material on said second side of said second portion of said elastic sleeve.

6. The knee brace according to claim 5, wherein at least an outer portion of said second flap of material comprises loop material; and wherein said hook material on said portion of said second surface of said first cinching strap is configured to releasably secure to said loop material on said outer portion of said second flap of material; and wherein at least an outer portion of said fourth flap of material comprises loop material; and wherein said hook material on said portion of said second surface of said second cinching strap is configured to releasably secure to said loop material on said outer portion of said fourth flap of material.

7. The knee brace according to claim 1, wherein each of said first cinching strap and said second cinching strap are formed of a flexible material.

8. The knee brace according to claim 7, wherein each of said first cinching strap and said second cinching strap are formed of an elastic material.

9. The knee brace according to claim 8, wherein each of said first flap material, said second flap material, said third flap material, and said fourth flap material are formed of a flexible material.

10. The knee brace according to claim 9, wherein each of said first flap material, said second flap material, said third flap material, and said fourth flap material are formed of an elastic material.

11. The knee brace according to claim 1, further comprising: an opening formed in said elastic sleeve, said opening being sized and positioned to accommodate the patella of the wearer therein.

12. The knee brace according to claim 11, further comprising: an annular patellofemoral pad configured to surround said opening to provide support to the patella portion of the knee joint of the wearer while said knee brace is worn.

13. The knee brace according to claim 12, further comprising: a second opening formed in said elastic sleeve, said second opening being sized and positioned to prevent gathering of said elastic sleeve on a back of the leg of the wearer when flexing the knee joint.

* * * * *